(12) United States Patent
Dougall

(10) Patent No.: US 6,884,598 B2
(45) Date of Patent: Apr. 26, 2005

(54) SCREENING ASSAYS FOR AGONISTS AND ANTAGONISTS OF RECEPTOR ACTIVATOR OF NF-κB

(75) Inventor: William C. Dougall, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 279 days.

(21) Appl. No.: 09/957,944

(22) Filed: Sep. 20, 2001

(65) Prior Publication Data

US 2002/0086312 A1 Jul. 4, 2002

Related U.S. Application Data

(60) Provisional application No. 60/235,157, filed on Sep. 22, 2000.

(51) Int. Cl.$^7$ .................................................. C12Q 1/66
(52) U.S. Cl. ........................... 435/8; 435/7.1; 435/7.2; 530/350; 536/23.5
(58) Field of Search .............................. 530/350; 435/6, 435/7.1

(56) References Cited

U.S. PATENT DOCUMENTS

| | | |
|---|---|---|
| 5,843,678 A | 12/1998 | Boyle |
| 6,015,938 A | 1/2000 | Boyle et al. |
| 6,017,729 A | 1/2000 | Anderson et al. |
| 6,171,860 B1 | 1/2001 | Baker et al. |
| 6,242,213 B1 | 6/2001 | Anderson |
| 6,242,586 B1 | 6/2001 | Gorman et al. |
| 6,284,485 B1 | 9/2001 | Boyle et al. |
| 6,316,408 B1 | 11/2001 | Boyle |
| 6,369,027 B1 | 4/2002 | Boyle et al. |
| 6,410,516 B1 | 6/2002 | Baltimore et al. |
| 6,492,124 B1 | 12/2002 | Wong et al. |
| 6,537,763 B1 * | 3/2003 | Dougall et al. ............... 435/7.1 |
| 2002/0068690 A1 | 6/2002 | Baldwin et al. |
| 2002/0127637 A1 | 9/2002 | Ni et al. |
| 2002/0159970 A1 | 10/2002 | Choi et al. |
| 2003/0013170 A1 | 12/2002 | Aggarwal et al. |
| 2003/0013651 A1 | 1/2003 | Lam et al. |

FOREIGN PATENT DOCUMENTS

| | | |
|---|---|---|
| EP | 0 418 014 | 12/1995 |
| EP | 0 873 998 | 10/1998 |
| EP | 0 911 342 | 4/1999 |
| EP | 1 087 230 | 3/2001 |
| JP | 11009269 A | 1/1999 |
| WO | WO 98/25958 | 6/1998 |
| WO | WO 98/46751 | 10/1998 |
| WO | WO 98/54201 | 12/1998 |
| WO | WO 99/29865 | 6/1999 |
| WO | WO 00/15807 | 3/2000 |
| WO | WO 00/75185 | 12/2000 |
| WO | WO 01/03719 | 1/2001 |
| WO | WO 01/08677 | 2/2001 |
| WO | WO 01/08699 | 2/2001 |
| WO | WO 01/16299 | 3/2001 |
| WO | WO 01/17543 | 3/2001 |
| WO | WO 01/18203 | 3/2001 |
| WO | WO 01/22090 | 3/2001 |
| WO | WO 01/23549 | 4/2001 |
| WO | WO 01/34827 | 5/2001 |
| WO | WO 01/62932 | 8/2001 |
| WO | WO 01/91793 | 12/2001 |
| WO | WO 02/15846 | 2/2002 |
| WO | WO 02/16551 | 2/2002 |
| WO | WO 02/064782 | 8/2002 |
| WO | WO 02/076507 | 10/2002 |
| WO | WO 02/080955 | 10/2002 |
| WO | WO 02/092623 | 11/2002 |
| WO | WO 02/095012 | 11/2002 |
| WO | WO 03/002713 | 12/2003 |

OTHER PUBLICATIONS

Takahashi N et al., "A new member of tumor necrosis factor ligand family, ODF/OPGL/TRANCE/RANKL, regulates osteoclast differentiation and function," *Biochem Biophys Res Commun* 1999; 256:449–455.

Tsukii K et al., "Osteoclast differentiation factor mediates an essential signal for bone resorption induced by 1α,25–dihydroxyvitamin $D_3$, prostaglandin $E_2$, or parathyroid hormone in the microenvironment of bone," *Biochem Biophys Res Commun* 1998; 246:337–341.

Childs L et al., "Safety and efficacy of RANK:Fc treatment for the prevention and amelioration of established osteolysis," 2001, Orthopedic Research Society, San Francisco, Abstract.

Darnay BG et al., "Characterization of the intracellular domain of receptor activator of NF–κB (RANK)," *J Biol Chem* Aug. 1998, 273(32):20551–20555.

Dougall W et al., "Rank is essential for osteoclast and lymph node development," *Genes Dev* 1999, 13:2412–2424.

Ducy P et al., "The osteoblast: a sophisticated fibroblast under central surveillance," *Science* Dec. 2000, 289:1501–1508.

Galibert L et al., "The involvement of multiple tumor necrosis factor receptor (TNFR)–associated factors in the signaling mechanisms of receptor activator of NF–κB, a member of the TNFR superfamily," *J Biol Chem* Dec. 1998, 273(51):34120–34127.

Hofbauer LC et al., "The roles of osteoprotegerin and osteoprotegerin ligand in the paracrine regulation of bone resorption," *J Bone Miner Res* Nov. 2000, 15:2–12.

(Continued)

Primary Examiner—Lorraine Spector
Assistant Examiner—Eileen B. O'Hara
(74) Attorney, Agent, or Firm—Diana K. Sheiness

(57) ABSTRACT

The present invention provides methods for screening for a molecule that antagonizes or agonizes RANK activity. One aspect of the invention involves the growth of RANK responsive cells in semi-solid medium, wherein exposure to a RANK antagonist promotes colony formation. Other aspects of the invention rely on promoter/reporter constructs using RANK responsive promoters derived from the MMP-9 and TRAP genes. Additional aspects of the invention exploit the ability of RANK to activate c-src activity, F-actin ring formation and $CaPO_4$ resorption.

25 Claims, No Drawings

OTHER PUBLICATIONS

Hsu H et al., "Tumor necrosis factor receptor family member RANK mediates osteoclast differentiation and activation induced by osteoprotegerin ligand," *Proc Natl Acad Sci USA* Mar. 1999;96:3540–3545.

Kodaira K et al., "Cloning and characterization of the gene encoding mouse osteoclast differentiation factor," *Gene* 1999, 230:121–127.

Lacey DL et al., "Osteoprotegerin ligand is a cytokine that regulates osteoclast differentiation and activation," *Cell* 1998, 93:165–176.

Lakkakorpi P and Vaananen, "Kinetics of the osteoclast cytoskeleton during the resorption cycle in vitro," *J Bone Min Res* 1991, 6(8):817–826.

Lee ZH et al., "Activation of c–Jun N–terminal kinase and activator protein 1 by receptor activator of nuclear factor κB," *Mol Pharmacol* 2000, 58(6):1536–1545.

Lowe C et al., "Osteopetrosis in Src–deficient mice is due to an autonomous defect of osteoclasts," *Proc. Natl. Acad. Sci. USA* 1993, 91:4485–4489.

Nakagawa N et al., "RANK is the essential signaling receptor for osteoclast differentiation factor in osteoclastogenesis," *Biochem Biophys Res Commun* 1998, 253:395–400.

Oyajobi BO et al., "A soluble murine receptor activator of NF–κB–human immunoglobulin fusion protein (RANK.Fc) inhibits bone resorption in a murine model of human multiple myeloma bone disease," *J Bone Min Res* Sep. 2000, 15(suppl. 1):S176, Abstract #1151.

Oyajobi BO et al., "Therapeutic efficacy of a soluble receptor activator of nuclear factor κB–IgG Fc fusion protein in suppression bone resorption and hypercalcemia in a model of humoral hypercalcemia of malignancy," *Cancer Res* Mar. 2001, 61:2572–2578.

Pearse RN et al., "Multiple myeloma disrupts the TRANCE/osteoprotegerin cytokine axis to trigger bone destruction and promote tumor progression," *PNAS* Sep. 2001. 98:11581–11586.

Rodan GA and Martin TJ, "Therapeutic approaches to bone diseases," *Science* Sep. 2000, 289:1508–1514.

Roodman D, "Advances in bone biology: the osteoclast," *Endocr Rev* 1996, 17:308–332.

Sato H et al., "v–Src activates the expression of 92–kDa type IV collagenase gene through the AP–1 site and the GT box homologous to retinoblastoma control elements," *J Biol Chem* Nov. 1993, 268(31): 23460–23468.

Shevde NK et al., "Estrogen inhibits RANKL stimulated osteoclastogenesis in isolated murine myeloid progenitors and the monocytic/macrophagic cell line RAW 264.7," *J Bone Min Res* 1999, 14(suppl.1):S150.

Simonet WS et al., "Osteoprotegerin: a novel secreted protein involved in the regulation of bone density," *Cell* Apr. 1997, 89:309–319.

Suda T et al., "Modulation of osteoclast differentiation," *Endocr Rev* Feb 1992, 13(2):66–80.

Takayanagi H et al., "Involvement of receptor activator of nuclear factor κB ligand/osteoclast differentiation factor in osteoclastogenesis from synoviocytes in rheumatoid arthritis," *Arthritis Rheum* Feb. 2000, 43(2):259–269.

Wong BR et al., "The TRAF family of signal transducers mediates NF–κB activation by the TRANCE receptor," *J Biol Chem* Oct. 1998, 273(43):28355–28359.

Wong BR et al., "TRANCE, a TNF family member, activates Akt/PKB through a signaling complex involving TRAF6 and c–Src," *Mol Cell* Dec. 1999, 4:1041–1049.

Yasuda H et al., "Osteoclast differentiation factor is a ligand for osteoprotegerin/osteoclastogenesis–inhibitory factor and is identical to TRANCE/RANKL," *PNAS* Mar. 1998, 95:3597–3602.

* cited by examiner

SCREENING ASSAYS FOR AGONISTS AND ANTAGONISTS OF RECEPTOR ACTIVATOR OF NF-κB

This application claims the benefit of priority from U.S. provisional patent application No. 60/235,157, filed Sep. 22, 2000, which is hereby incorporated by reference in its entirety.

FIELD OF THE INVENTION

This invention relates to methods for screening for agonists and/or antagonists of activities associated with receptor activator of NF-κB (RANK).

BACKGROUND OF THE INVENTION

RANK, an acronym for receptor activator of NF-κB, is a Type I transmembrane protein that is a member of the tumor necrosis factor (TNF) receptor superfamily and which when triggered activates the transcription factor NF-κB (Anderson et al., Nature 390:175–179 (1997); Anderson et al., U.S. Pat. No. 6,017,729). The human RANK (616 amino acids) has a signal peptide (28 amino acids), an N-terminal extracellular domain (184 amino acids), a short transmembrane domain (21 amino acids), and a large C-terminal cytoplasmic domain (383 amino acids), and mouse RANK is similarly arranged (Anderson et al., 1997). The extracellular domain of RANK contains four cysteine-rich pseudorepeats and two N-glycosylation sites, which features are characteristic of members of the TNF receptor superfamily. RANK has a 40% homology with CD40 (Anderson et al., 1997), and is expressed on T cells, dendritic cells, and osteoclasts (Anderson et al., 1997; Hofbauer et al., J Bone Min Res 15:2–12 (2000)).

The cytoplasmic domain of RANK associates intracellularly with several of the TNF receptor-associated factors (TRAFs; Baker and Reddy, Oncogene 12:1 (1996)) including TRAF1, TRAF2, TRAF3, TRAF5, and TRAF6 (Galibert et al., J Biol Chem 273:34120–27 (1998)). These TRAF binding sites are clustered in two distinct domains in the RANK cytoplasmic tail. The TRAFs are cytoplasmic proteins that often mediate signal transduction by members of the TNF receptor superfamily, and they are important in the regulation of, for example, immune and inflammatory responses. RANK mediates some or all of its biological activities through a cascade of events that involves the TRAF binding sites (see, for example, Galibert et al., 1998).

Triggering of RANK, such as by contact with membrane-bound or soluble RANK-L, results in the stimulation of RANK-mediated cellular responses. These cellular responses can include the activation of transcription factor NF-κB, a ubiquitous transcription factor that is extensively utilized in cells of the immune system, or the activation of Jun kinase (JNK; see, for example, Galibert et al., 1998). RANK activation in osteoclast progenitor cells induces the progenitors to differentiate into mature osteoclasts. This differentiation process is accompanied by the rearrangement of actin into "F-actin rings," a specialized structure that is detectable by staining (Lakkakorpi, P. and Vaananen, J. Bone Min Res 6:817–826 (1991)). Elevated levels of c-src tyrosine kinase activity is also associated with RANK activation (Wong et al. Molecular Cell 4:1041–1049 (1999)).

RANK ligand (RANK-L) is a cell surface protein that binds with and activates RANK (Anderson et al., U.S. Pat. No. 6,017,729). This protein is also known as TRANCE, ODF or OPG ligand (Wong et al., 1999). RANK-L is a Type 2 transmembrane protein, and has an intracellular domain of about 50 amino acids or less, a transmembrane domain and an extracellular domain of about 240 to 250 amino acids. The extracellular domain of RANK-L contains a RANK-binding site. Similar to other members of the TNF family to which it belongs, RANK-L has a "spacer" region between the transmembrane domain and the receptor binding domain that is not necessary for receptor binding.

In bone, RANK-L stimulates osteoclast differentiation, enhances the activity of mature osteoclasts, and inhibits osteoclast apoptosis, thereby expanding the pool of activated osteoclasts (see, for example, Hsu et al., Proc Nat'l Acad Sci USA. 96:3540–45 (1999)). Osteoclasts are large, phagocytic, multinucleated cells which are formed from hematopoietic precursor cells in the bone marrow. Osteoclasts promote dissolution of the bone matrix and solubilization of bone salts, and are required for the proper development and growth of bones.

RANK knock-out mice are severely osteopetrotic and lack peripheral lymph nodes (Dougall et al., Genes Dev. 13:2412–24 (1999)). Modulation of RANK and RANK-L activity has been proposed as a means for treating a variety of disorders that involve osteopenia or osteopetrosis, including, for example, osteoporosis, Paget's disease, hypercalcemia, and so on (see, for example, WO 98/46751 and WO 99/58674).

RANK and its ligand play an integral role in the regulation of a wide range of biological systems, including the immune response, the inflammatory response, and bone remodeling through activation of osteoclasts. In view of the importance of RANK in the regulation of a wide range of biological systems, there is a need for methods for screening for molecules that antagonize or agonize RANK activity.

SUMMARY OF THE INVENTION

The present invention provides methods for screening for a molecule that antagonizes or agonizes RANK activity.

In one embodiment of the invention, assays for RANK agonists or antagonists involve culturing RANK responsive cells in a semi-solid medium in the presence of a candidate molecule and determining whether compared with a control culture the rate of colony formation or rate of colony growth is enhanced or reduced in cells that have been contacted with the candidate molecule. In this assay, a candidate molecule is identified as being a RANK antagonist if the rate of colony formation or colony growth in the contacted cells, also called "test cells," is enhanced as compared with the rate of colony formation or growth in the control reference cells that are not contacted with the candidate molecule, or as a RANK agonist if the rate is comparatively reduced. Except for contact with the candidate molecule, control reference cells are otherwise cultured and handled in the same manner as the test cultures.

In one aspect of the invention, the semi-solid medium used is methylcellulose, though soft agar, soft agarose or the like also may be used.

If desired, candidate molecules can be batched for this assay. In this approach, a plurality of candidate molecules are added to a test culture. If RANK activity modulation is observed in such cultures, each candidate molecule in the batch can then be tested separately and antagonists or agonists identified individually.

When the semi-solid medium assay is used to screen for molecules that antagonize RANK activity, RANK is triggered in the RANK responsive cells before, during and/or after the exposure of the test cells to the candidate molecule. As used herein, RANK triggering refers to some event that stimulates the RANK protein to transduce a signal to the cell in which it is being expressed. Cells useful in this first aspect of the invention express RANK protein, are capable of forming colonies in a semi-solid medium, and are stimulated by the action of one or more RANK-mediated cellular signaling pathways to differentiate into cell types that cannot form colonies in semi-solid medium.

When RANK activity is stimulated in RANK responsive cells for the semi-solid medium assays of the invention, preferred methods of stimulation include: contacting the RANK responsive cells with a RANK-L polypeptide, such as a RANK-L polypeptide comprising amino acids 162–317 of SEQ ID NO:6 or amino acids 161–316 of SEQ ID NO:8; contacting the RANK responsive cells with agonistic anti-RANK antibodies; contacting the RANK responsive cells with one or more cells that express a RANK-L polypeptide; overexpressing RANK in the RANK responsive cells; and expressing in the RANK responsive cells a mutant form of RANK that induces RANK signaling at normal levels of RANK expression in the absence of RANK-L. An example of the latter type of RANK is FEO RANK (SEQ ID NOS:9 and 10).

Exemplary RANK-L polypeptides for stimulating RANK activity include native RANK-L, such as endogenous RANK-L that is expressed on the surfaces of cells, soluble forms of RANK-L, a leucine zipper fusion of RANK-L, and a FLAG™ polyHis fusion of RANK-L. Another method for stimulating RANK activity for the subject assays is to contact the RANK responsive cells with an agonistic anti-RANK antibody. Exemplary agonistic anti-RANK antibodies for this purpose include M330 antibodies and M331 antibodies, both of which are directed against human RANK, and M395 and M396 antibodies, which are directed against murine RANK.

In one aspect of the invention, the rate of colony formation or colony growth in semi-solid medium is determined by visual inspection of the plates after the cells have been exposed to the candidate molecules. The numbers of colonies or sizes of observed colonies is compared for plates exposed to the candidate molecule and similar cultures not exposed to the candidate molecules.

One means of contacting the RANK responsive cells with a candidate molecule involves introducing into the test cells a DNA molecule that encodes either a candidate nucleic acid molecule or that encodes a candidate protein molecule. For example, the introduced DNA can be a cDNA molecule encoding a single protein or a cDNA library encoding a group of proteins to be tested. After being introduced into the cell, this DNA may or may not become integrated into the genome of the RANK responsive cells. Techniques for stable transfection and transient transfection are known, and either type of technique may be used. In some instances, the encoded candidate molecule is a nucleic acid molecule, such as an anti-sense oligonucleotide or an RNA with ribozyme activity. In one aspect of the invention, cDNAs determined to encode a RANK agonist or antagonist are isolated and purified from colonies of test cells that are growing in semi-solid medium.

Other means of contacting the RANK responsive cells with candidate molecules involve adding the candidate molecule directly to the semi-solid medium, either by mixing it with the medium before pouring the plates, or by overlaying the poured plates with a layer of medium containing the candidate molecule. For example, the foregoing methods may be used when the candidate molecule is a protein or small organic molecule. If desired, a plurality of proteins or other test molecules may be added to the test cultures.

In one aspect of the invention, RANK responsive cells are employed that express a defective RANK molecule and the screening is for an agonist that complements this defective RANK molecule. An exemplary defective RANK for this purpose is human RANKΔ340–42.

Suitable RANK responsive cells for the above described assays include primary hematopoietic cells, including hematopoietic precursor cells derived from bone marrow, spleen, fetal liver or peripheral blood, as well as primary hematopoietic cells derived from bone marrow, spleen, fetal liver or peripheral blood and enriched for osteoclast precursors. In other aspects of the invention, the RANK responsive cells are a cell line. Suitable cell lines include RAW 264.7 cells, C7 cells, and BCL-X1/Tag cells.

Another aspect of the invention exploits the ability of promoter sequences derived from the tartrate-resistant acid phosphatase (TRAP) gene (SEQ ID NO:12) or the MMP-9 gene (SEQ ID NO:11) to respond directly to signal transduction resulting from RANK triggering. In a preferred embodiment, the MMP-9 promoter comprises nucleotides 1769–3591 of SEQ ID NO:11. The present invention provides methods for screening for a RANK agonist or antagonist by employing recombinant DNA constructs in which a TRAP or MMP-9 promoter is operably linked to a nucleic acid molecule that encodes a reporter protein. Reporter proteins suitable for this purpose include, for example, luciferase, β-galactosidase, green fluorescent protein, alkaline phosphatase or a heterologous surface protein detectable by antibody binding methods. Examples of the latter include human IL-2 receptor, murine IL-4 receptor, human CD2 protein, human CD4 protein and human CD8 protein.

For these assays, a reporter/promoter construct as described herein is introduced into cultured RANK responsive cells. Suitable RANK responsive cells include hematopoietic cells. Examples of suitable hematopoietic cells include RAW 264.7 cells. To use this approach to screen for a RANK antagonist, the constructs are introduced into the test cells, which then are treated with a RANK activity agonist, such as soluble RANK-L, which triggers RANK in the cells, thereby activating the promoter activity in the construct, resulting in expression of the reporter gene. Candidate antagonist molecules are contacted with the triggered cells to test for their ability to suppress this RANK-mediated reporter gene expression. The test cells are contacted with the candidate antagonist before, during or after the RANK triggering step.

Candidate molecules, for example, may be added to the culture medium. In one embodiment of the invention, the candidate molecule is a protein; in another embodiment it is a small organic molecule.

In one aspect of the invention, the candidate molecule is a protein or group of proteins encoded by cDNA that is introduced into the test cells prior to cells' being exposed to the RANK trigger. Generally, the cDNA is introduced at least 48 hours prior to triggering RANK. The cDNA can be isolated from cells that exhibit an altered level of reporter gene expression.

Suitable methods for triggering RANK in the above-described reporter/promoter construct assays include exposing the test cells to cells that express RANK-L on their surfaces, exposing the test cells to soluble RANK-L, overexpressing RANK in the test cells, expressing human RANKΔ340–42 in the test cells, or exposing the test cells to an agonistic antibody specific for the RANK protein. In one aspect of the invention, RANK is triggered in the RANK responsive cells by contacting them with a RANK-L polypeptide that includes amino acids 162–317 of SEQ ID NO:6 or amino acids 161–316 of SEQ ID NO:8.

Test cells in which RANK has been triggered are contacted with the candidate molecule and the cells then are analyzed to determine whether the level of reporter protein expression is enhanced or reduced as a result of this contact. The level of reporter expression is determined by any suitable assay, such as a fluorescence-based assay, a colorimetric assay, a solid phase assay, or assays employing a radioactive compound. One means of determining levels of reporter gene product is to use conventional methods to physically isolate by fluorescence-based cell sorting those cells that are expressing the reporter molecule. Enhancement or reduction of reporter protein expression in the test cells is determined by comparing the level of reporter protein expression in the test cells with the level of expression in control cultures that are not contacted with the candidate molecule. If the candidate molecule is a RANK antagonist, the level of reporter expression will be comparatively reduced.

The above-described constructs also are used to screen for RANK agonists. In this instance, RANK is not deliberately triggered in the test cells, but rather the candidate molecule is assessed for its ability to trigger RANK. Cells useful in this aspect of the invention express RANK protein and contain at least one signal transduction pathway that is stimulated by the activation of RANK. In some instances, the agonist is contacted with the cells by introducing into the cells a cDNA encoding a candidate protein agonist, or by introducing a cDNA library encoding a plurality of candidate protein agonists. In such instances, an agonist can be isolated by recovering and purifying the cDNA from those colonies that exhibit enhanced reporter gene expression. Furthermore, it can be demonstrated using conventional techniques that the purified candidate molecule indeed interacts with RANK.

In one aspect of the invention, the reporter/promoter constructs are used to identify RANK agonists by using cells that express a defective RANK molecule and the screening is for an agonist that complements the defective RANK activity. For example, cells expressing human RANKΔ340–42 may be used for this purpose.

In another aspect of the invention, screening for antagonists or agonists of RANK activity involves contacting a candidate molecule with RANK responsive cells that are capable of differentiating into osteoclasts in response to the triggering of RANK. To screen for RANK antagonists, one triggers RANK in the cells, exposes the cells to the candidate antagonist, and observes the level of c-src activity or F-actin formation as compared to the level of c-src activity or F-actin formation in reference RANK responsive cells that are not contacted with the candidate molecule. If the candidate is an antagonist, the rate of c-src activity and F-actin ring formation will be comparatively reduced. If the candidate is to be screened for RANK agonist activity, the RANK triggering step is omitted and a positive result will consist of observing enhanced c-src activation and F-actin formation.

In yet another aspect of the invention, candidate RANK agonists or antagonists are screened by contacting a candidate molecule with RANK responsive cells that are capable of differentiating into osteoclasts in response to the triggering of RANK in said cells, triggering RANK in the cells, then culturing the cells on a film of $CaPO_4$. Differentiated osteoclasts will resorb the $CaPO_4$ in their immediate vicinity, thus producing a pit in the film. One then compares the number of pits in the film that are caused by the contacted cultured cells versus the number of pits caused in a similar film by reference RANK responsive cells in which RANK is triggered but which are not contacted with the candidate molecule. One then can identify a candidate molecule as a RANK agonist if a greater number of pits is caused by the candidate molecule-treated cells than by the reference cells and as a RANK antagonist if the number of pits caused by the treated cells is less than the number caused by the control cells.

DETAILED DESCRIPTION OF THE PREFERRED EMBODIMENT

The present invention provides methods for screening for a molecule that antagonizes or agonizes RANK activity. Although various assays for detecting antagonists and agonists of RANK are known in the art (see, for example, U.S. Pat. No. 6,017,729), the screening strategies described herein have not been previously described.

As used herein, the term "RANK agonist," or grammatical equivalents thereof, refers to a molecule that stimulates RANK activity, including a molecule that triggers RANK. A RANK agonist can interact directly with RANK, or may enhance RANK activity indirectly. RANK-L, for example, would be considered to be a RANK agonist. Also, antibodies that specifically bind RANK often act as agonists of RANK activity.

As used herein, the term "RANK antagonist," or grammatical equivalents thereof, refers to a molecule that inhibits RANK activity. A RANK antagonist can interact directly or indirectly with RANK. RANK:Fc (described in U.S. Pat. No. 6,017,729) and osteoprotegerin (described in U.S. Pat. No. 6,015,938) are examples of RANK antagonists, the former being a fusion protein containing the extracellular domain of RANK fused with the Fc region of immunoglobulin, and the latter being a naturally-occurring protein. These two proteins antagonize RANK by binding RANK-L, thereby preventing the RANK-L from binding with RANK responsive cells.

The term "RANK" as used herein refers to a protein having the ability to activate NF-κB or the ability to bind with TRAF1, TRAF2, TRAF3, TRAF5 or TRAF6, and having an at least 80% amino acid identity with the amino acid sequence shown in SEQ ID NO:2 or SEQ ID NO:4. RANK proteins according to the invention are capable of binding with antibodies that bind specifically to a protein having the amino acid sequence of SEQ ID NO:2 or SEQ ID NO:4.

The term "RANK-L" is an acronym for RANK ligand, which is a Type 2 transmembrane protein that binds to and activates RANK. The sequences of two nucleic acid molecules encoding representative RANK-L proteins are set forth in SEQ ID NO:5 (human RANK-L) and SEQ ID NO:7 (murine RANK-L), and the sequences of the RANK-L proteins encoded by these two nucleic acid sequences are set forth in SEQ ID NO:6 and SEQ ID NO:8, respectively. It is understood that "RANK-L" as used herein includes both full-length RANK-L proteins as well as membrane-bound or soluble forms of the RANK-L protein, including chimeric molecules comprising portions of RANK-L and multimeric RANK-L molecules.

RANK and RANK-L are involved in controlling formation of mature osteoclasts, the primary cell type implicated in bone resorption. An increase in the rate of bone resorption (over that of bone formation) can lead to various bone disorders which are collectively referred to as osteopenias, and include osteoporosis, osteomyelitis, hypercalcemia, osteopenia brought on by surgery or steroid administration, Paget's disease, osteonecrosis, bone loss due to rheumatoid arthritis, periodontal bone loss, prosthetic loss or loosening and osteolytic metastasis. Agonists and antagonists of RANK can be used to modulate osteoclast formation and may be administered to patients suffering from bone disorders to ameliorate these conditions.

Further, many cancers metastasize to bone and induce bone breakdown by locally disrupting normal bone remodeling. Such cancers can be associated with enhanced numbers of osteoclasts and enhanced amount of osteoclastic bone resorption resulting in hypercalcemia (see, for example, Guise et al. *Endocrine Reviews*, 19(1):18–54, 1998.). Other cancers do not necessarily metastasize to bone, but result in hypercalcemia and bone loss (e.g., squamous cell carcinomas). Agonists and antagonists of RANK may be administered to patients suffering from cancer to ameliorate the symptoms thereof, including but are not limited to those suffering from breast cancer, multiple myeloma, melanoma, lung cancer, prostate, hematologic, head and neck, and renal cancer. Antagonists of the RANK/RANKL interaction are particularly useful for treating cancer.

In addition, RANK antagonists or agonists identified by the present screening assays can be used to prevent or treat cardiovascular diseases and other conditions characterized by arterial calcification. Also, the antagonists and agonists of RANK identified herein are useful in treating immune diseases and/or inflammatory diseases, such as toxic or septic shock, or graft-versus-host reactions (such as via the inhibition of NF-PB activation). As RANK triggering stimulates T cell activation, the RANK agonists identified herein are useful as vaccine adjuvants.

Tumor cells are more responsive to radiation when their NF-κB is blocked; thus, antagonists of RANK signaling will be useful as an adjunct therapy for disease characterized by neoplastic cells that express RANK. Conversely, agonists of RANK will be useful for stimulating RANK-mediated cellular responses, and certain RANK agonists may be capable of complementing inactive RANK mutants.

Candidate Molecules to be Tested for RANK Agonist or Antagonist Activity:

Examples of candidate molecules, also referred to herein as "test molecules," to be tested for RANK agonist or antagonist activity include, but are not limited to, carbohydrates, small molecules (usually organic molecules or peptides), proteins, and nucleic acid molecules (including oligonucleotide fragments typically consisting of from 8 to 30 nucleic acid residues). Peptides to be tested typically consist of from 5 to 25 amino acid residues. Also, candidate nucleic acid molecules can be antisense nucleic acid sequences, and/or can possess ribozyme activity. If desired, antisense or ribozyrne RNAs can be introduced into a target cell by means of introducing into the cells a DNA molecule that encodes the antisense or ribozyme RNA.

Small molecules to be screened using the hereindescribed screening assays can typically be administered orally or by injection to a patient in need thereof. Small molecules that can be administered orally are especially preferred. The small molecules of the invention preferably will not be toxic at the doses required for them to be effective as pharmaceutical agents, and they are preferably not subject to rapid loss of activity in the body, such as the loss of activity that might result from rapid enzymatic or chemical degradation. In addition, pharmaceutically useful small molecules are preferably not immunogenic.

The methods of the invention can be used to screen for antisense molecules that inhibit RANK activity by virtue of interfering with the functional expression of one or more mRNA molecules that encode one or more proteins that mediate a RANK-dependent cellular response. An anti-sense nucleic acid molecules are complementary to a nucleic acid target expressed within the host cell and by forming duplexes with the target thus hinder the target from functioning. Anti-sense nucleic acids may block the transcription of a target gene by duplexing with either strand of the DNA encoding the gene, or by duplexing with a regulatory element that controls expression of the target gene. Alternatively, it may duplex with an mRNA, thus hindering or blocking its translation. An anti-sense nucleic acid molecule may be constructed in a number of different ways provided that it is capable of interfering with the expression of a target gene. Typical anti-sense oligonucleotides to be screened preferably are 20–50 nucleotides in length, and more preferably are 30–40 nucleotides in length. The anti-sense nucleic acid molecule generally will be substantially identical in nucleotide sequence to one strand of the target gene. The minimal identity will typically be greater than about 65%, but a higher identity might exert a more effective repression of expression of the endogenous sequences. Substantially greater identity of more than about 80% is preferred, though about 95% to absolute identity is most preferred.

Candidate nucleic acid molecules can possess ribozyme activity. Thus, the methods of the invention can be used to screen for ribozyme molecules that inhibit the functional expression of one or more mRNA molecules that encode one or more proteins that mediate a RANK dependent cellular response. Ribozymes are catalytic RNA molecules that can cleave nucleic acid molecules having a sequence that is completely or partially homologous to the sequence of the ribozyme. It is possible to design ribozyme transgenes that encode RNA ribozyrnes that specifically pair with a target RNA and cleave the phosphodiester backbone at a specific location, thereby functionally inactivating the target RNA. In carrying out this cleavage, the ribozyme is not itself altered, and thus is capable of continuing to cleave other target RNA molecules. The inclusion of ribozyme sequences within antisense RNAs confers RNA-cleaving activity upon them, thereby increasing the activity of the antisense constructs.

The design and use of target RNA-specific ribozymes is described in Haseloffet al. (*Nature*, 334: 585–591(1988)) (see also U.S. Pat. No. 5,646,023), both of which publications are incorporated herein by reference. Tabler et al. (*Gene* 108:175 (1991)) have greatly simplified the construction of catalytic RNAs by combining the advantages of the anti-sense RNA and the ribozyme technologies in a single construct. Smaller regions of homology are required for ribozyme catalysis, therefore this can promote the repression of different members of a large gene family if the cleavage sites are conserved.

RANK and RANK-L Molecules

Generally, the screening assays described herein involve a RANK or a RANK-L protein.

RANK and its binding partner RANK-L and nucleic acids encoding these proteins are known in the art and have been well-characterized with respect to their physical properties, their disposition within the cell, and with respect to may of the biological activities associated with the binding of RANK and RANK-L. Examples of murine and/or human RANK as well as examples of murine and/or human RANK-L are disclosed in U.S. Pat. No. 6,017,729, U.S. Pat.

No. 5,843,678 (disclosing "osteoprotegerin binding protein," which is described herein as murine RANK-L), WO 98/25958 (disclosing "488E9, " which is described herein as murine RANK-L); WO 98/44751 (disclosing murine "ODAR," referred to herein as murine RANK); and EP 0 911 342 (disclosing "OCIF-binding molecule," referred to herein as murine RANK-L). Others have disclosed RANK-L, referring to it as "TRANCE" (see, for example, Wong et al., Molec Cell 4:1041–49 (1999)). Any of these RANK and RANK-L molecules may be used in the assays described herein.

The sequences of two nucleic acid molecules encoding representative RANK proteins are set forth in SEQ ID NO:1 (human RANK) and SEQ ID NO:3 (murine RANK), and amino acid sequences encoded by these nucleic acid molecules are set forth in SEQ ID NOS:2 and 4, respectively. The sequences of exemplary human and mouse RANK-L sequences are shown in SEQ ID NOS:6 and 8, and nucleic acids encoding these proteins in SEQ ID NOS:5 and 7. However, it is understood that other RANK and RANK-L variants other than those shown in these examples may be used in the hereindisclosed assays, including other RANK and RANK-L molecules known in the art, or variants having amino acid differences that do not influence the binding of RANK to RANK-L nor the triggering of RANK that normally results from this binding.

Sequence variants of native RANK and RANK-L polypeptides are useful in the practice of the present invention in any instance where the native RANK or RANK-L polypeptide is utilized, provided that the variant possesses any biological activity required for the assay. Generally for these assays, suitable RANK variants will bind RANK-L thereby stimulating RANK activity, and suitable RANK-L variants will bind to RANK thereby stimulating RANK activity. Mutations present in such variants may include, for example, substitutions, deletions, and insertions of amino acids. Allelic forms or mutated forms of RANK and RANK-L can be obtained for use in these assays by using a variety of techniques known in the art, including, for example, site-directed mutagenesis, oligonucleotide-directed mutagenesis, and so on.

RANK molecules useful for the disclosed methods include wild-type RANK as well as variant forms of RANK. The variants may differ in amino acid sequence from the RANK molecules of SEQ ID NOS:2 or 4, but will retain the ability to transduce at least one of the biological signals that is associated with the triggering of wild-type RANK, such as activation of NF-κB. Suitable variants include naturally-occurring allelic variants, mutant forms of RANK (such as FEO RANK) or variants constructed using recombinant DNA technology.

RANK-L proteins, including soluble forms of RANK-L, useful for triggering RANK will contain the RANK binding domain, which is contained in the extracellular region of the molecule. For human RANK-L, the extracellular domain encompasses about 249 amino acids at the carboxy end of the protein (amino acids 69 through 317 of SEQ ID NO:6), and for mouse RANK-L encompasses about 247 amino acids at the carboxy terminus of the protein (amino acids 70–316 of SEQ ID NO:8). Soluble RANK-L for triggering RANK may comprise the entire extracellular region, or may comprise only that portion of RANK-L that contains the RANK-binding domain, which for human RANK-L is found in a fragment having amino acids 69 to 317 of SEQ ID NO:6, or more preferably having amino acids 162–317 of SEQ ID NO:6, or for murine RANK-L in a fragment having amino acids 70 to 316 of SEQ ID NO:8, or more preferably having amino acids 161–316 of SEQ ID NO:8.

Soluble RANK-L for triggering RANK may further comprise a signal peptide that directs secretion of the soluble protein, and also may further comprise a second polypeptide, such as, for example, a polypeptide which when present will stimulate oligomerization of the soluble RANK-L fusion protein. RANK-L fragments for constructing soluble RANK-Ls can be prepared using known recombinant techniques to isolate a desired portion of the extracellular region. Various RANK-L derivatives for triggering RANK include covalent or aggregative conjugates of the proteins or their fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-translationally directs transfer of the protein from its site of synthesis to its site of function outside of the cell membrane or wall (e.g., the yeast α-factor leader). Alternatively, RANK-L may be conjugated in some instances with a poly-His or FLAG® tag as described in U.S. Pat. No. 6,017,729.

Generally, if RANK-L is being used to trigger RANK, the RANK-L is derived from the same species (for example, human) from which the RANK is derived. However, mouse RANK-L is capable of triggering human RANK, and human RANK-L is capable of triggering mouse RANK.

RANK proteins useful in the practice of the present invention typically have an amino acid sequence that is at least 80% identical, or at least 85% identical, or preferably at least 90% identical to all or a portion of the native RANK amino acid sequences set forth in SEQ ID NOS:2 or 4. RANK-L proteins useful in the practice of the present invention typically have an amino acid sequence that is at least 80% identical, or at least 85% identical, or preferably at least 90% identical to all or a portion of the native RANK-L amino acid sequences set forth in SEQ ID NOS:6 or 8. The RANK proteins of the invention when triggered are capable of activating NF-κB activity.

Percent identity is determined as follows. Amino acid sequence identity is defined as the percentage of the amino acid residues set forth in SEQ ID NOS:2, 4, 6 or 8 that are identical with part or all of another protein sequence (which may be a portion of a larger protein sequence) after aligning the sequences and introducing gaps, if necessary, to achieve the maximum percent identity. For comparing amino acid sequences of unequal length, the percent identity is calculated based on the smaller of the two sequences. Percent identity may be determined using a computer program, for example, the GAP computer program described by Devereux et al. (Nucl. Acids Res 12:387, 1984), which is available from the University of Wisconsin Genetics Computer Group (UWGCG), or any other suitable computer program that is capable of aligning and comparing two or more amino acid sequences. When using the GAP program, preferred default parameters for conducting the comparison include: (1) a unary comparison matrix (containing a value of 1 for identities and 0 for non-identities) for amino acids, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353–358, 1979; (2) a penalty of 3.0 for each gap and an additional 0.10 penalty for each symbol in each gap; and (3) no penalty for end gaps. Another program useful for determining percent identify is the BESTFIT program, also available from the University of Wisconsin as part of the GCG computer package. Default parameters for using the BESTFIT program are the same as those described above for using the GAP program.

Some embodiments of the invention employ mutant forms of the RANK protein. An example of this type of RANK mutant is the mutated form of RANK isolated from patients having a condition known as "familial expansile osteolysis" (FEO), which is a rare autosomal dominant bone dysplasia with similarities to Paget's disease of bone. These diseases are characterized by focal areas of increased bone remodeling that leads to deformity and disability. The FEO gene and the gene associated with familial Paget's disease of the bone map to chromosome 18q21 which is the same location that includes the RANK gene. An exemplary FEO RANK DNA is described in Hughes et al., *Nat Genet* 24:45–48 (2000).

Mutant forms of RANK are especially useful in assays designed to identify molecules capable of complementing the defect in cells expressing this form of RANK, as such molecules can serve as therapeutic agents to treat diseases associated with the RANK mutation. The assays described herein are useful for screening for molecules that possess the capacity to complement the RANK defect in the FEO RANK gene. The sequences for an FEO RANK are given in SEQ ID NOS:9 and 10. Molecules with this capacity are "FEO RANK agonists" and will be useful for treating patients suffering from FEO, Paget's disease or related diseases, or for developing agents to be used for this purpose. It is anticipated that RANK mutations will be found to play a role in bone diseases other than FEO and Paget's. DNA encoding these mutated forms of RANK will be isolated and tested in the hereindescribed screening assays to identify treatments for the diseases.

RANK Activation:

Many of the assays described herein involve the use of RANK responsive cells. As used herein, the phrase "RANK responsive cell" refers to a cell that expresses a membrane-bound RANK protein that is capable of transducing an intracellular signal or stimulating a discernable biological response in the cell (such as differentiation from one cell type into another cell type) when the RANK protein is triggered by binding to a RANK-L or when the RANK is triggered by some other means.

As used herein, the phrase "RANK activity" refers to the biological activity in the cell that occurs after RANK itself has undergone activation, that is, after the RANK has become "triggered." In general, "RANK activity" is instigated by triggering RANK, and the RANK activity is detected by measuring one or more of the biological responses that is characteristically induced directly or indirectly by a triggered wild-type RANK protein. When RANK is triggered, it oligomerizes with other RANK molecules in its immediate vicinity in the cell membrane. If, for example, a RANK-specific agonistic antibody is used to trigger RANK, the antibody brings two RANK molecules into close proximity, thus allowing them to dimerize, thereby triggering RANK activity. It is possible that more than two RANK molecules will oligomerize when RANK is triggered. Probably, the oligomerization stimulates a conformational change in the cytoplasmic tail of the RANK protein, thereby initiating a chain of events that results in a discernable biological response.

Triggering RANK is a step required for many of the screening assays described herein, particularly when it is desired to screen for RANK antagonists. This may be accomplished in many different ways, including exposure to a RANK-L protein that possesses a RANK binding domain. Full-length RANK-L may be used, such as membrane-bound RANK-L, or soluble RANK-L molecules, such as the ones described above. At a minimum, the RANK-L polypeptide must be able to bind RANK, thus must possess that portion of the RANK-L extracellular region that has this capacity. One example of a type of RANK-L useful to stimulate RANK activity is a leucine zipper fusion of RANK-L, such as the leucine zipper fusion of RANK-L described in U.S. Pat. No. 6,017,729, or other leucine zipper constructs as described in that reference or elsewhere.

Another example of a type of RANK-L useful to stimulate RANK activity is a FLAG™ poly-His fusion of RANK-L, such as the FLAG™ poly-His fusion of RANK-L described in U.S. Pat. No. 6,017,729.

RANK can be triggered in a variety of ways, including but not limited to: over-expression of RANK in a cell; co-expression in the same cell of RANK and RANK-L; contacting cells expressing membrane-bound RANK with soluble RANK-L; contacting RANK-expressing cells with cells that express membrane-bound RANK-L; and adding agonistic antibodies directed against RANK to cells that are expressing RANK. In addition to the foregoing, any other desired method of triggering RANK may be used in the hereindisclosed assays.

One preferred method of triggering RANK is to contact RANK responsive cells with agonistic anti-RANK antibodies, i.e., antibodies that bind to RANK and stimulate RANK activity. Examples of agonistic anti-RANK antibodies include anti-human M330 antibodies, anti-human M331 antibodies, anti-mouse M395 antibodies, and anti-mouse M396 antibodies.

Yet another way to stimulate RANK activity in RANK responsive cells is to contact RANK responsive cells with one or more cell types expressing RANK-L, such as cells that express RANK-L on their surface or that secrete a soluble RANK-L protein. For example, RANK responsive cells can be co-cultured in liquid or semi-solid medium with one or more cell lines expressing RANK-L. Representative examples of cell types that express RANK-L include any cell type that is transfected with a nucleic acid molecule that encodes RANK-L cDNA (either transiently or stably) under conditions that enable the functional expression of RANK-L by the transfected cells. Additional examples of cell types that express RANK-L include primary T-cells (activated with anti-CD3 antibodies), B-cells (such as the 70z3 cell line), and the mouse thymoma cell line EL-4 (Anderson et al., Nature 390:175–179 (1997)). In addition, a number of osteoblast and bone marrow stromal cells of both human and mouse origin express RANK-L, including ST2 (Yasuda et al., Proc. Nat'l. Acad. Sci USA 95: 3597–3602 (1998)) and MC3T3-E1, hMS (Hofbauer et al., J. Bone Min. Res. 15: 2–12, 2000) as well as osteosarcoma cell lines ROS and MG-63 (Hofbauer et al., 2000). Expression of RANK-L can be upregulated in these aforementioned cell types using bone resorbing factors such as glucocorticoids, 1,25-dihydroxyvitamin D3, interleukin 1 (IL-1), IL-6, IL-17, TNFα, prostaglandin E2 or parathyroid hormone (see Hofbauer et al., 2000).

Also, cells which express a soluble RANK-L can be cultured on the solid surface of a culture well and RANK responsive cells, resuspended in semi-solid medium, are overlaid on top of the RANK-L expressing cells. RANK in these RANK responsive cells becomes triggered by contact with RANK-L that is secreted into and that diffuses throughout the semi-solid medium.

In some embodiments, the cells expressing RANK-L secrete a soluble form of the molecule. Representative examples of cell types that secrete soluble RANK-L include primary T-cells activated with anti-CD3 and/or anti-CD28 antibodies (Kong et al., Nature 402: 304–309 (1999)), and human 293 fibroblasts transfected with a nucleic acid molecule encoding RANK-L (Lacey et al., Cell 93: 165–178 (1998)).

Yet another way of stimulating RANK activity in RANK responsive cells is to overexpress RANK in the RANK responsive cells, for example by genetically transforming RANK responsive cells with a DNA construct that includes a nucleic acid sequence encoding RANK under the control of a strong, constitutive promoter. For example, in the absence of exogenously added RANK-L, 293/EBNA cells transfected with an expression vector (pDC409-hRANK) activate NF-κB activity (see, Anderson et al., 1997, supra) and an NF-κB responsive promoter-reporter as a result of RANK overexpression (see Galibert et al., J. Biol. Chem. 273:34120–27 (1998)). The concentration of RANK in the membrane of cells overexpressing RANK is so high that RANK spontaneously oligomerizes in these membranes, thereby triggering RANK activity. Suitable RANK nucleic acids for use in constructs to induce RANK overexpression include DNAs capable of encoding the RANK proteins shown in SEQ ID NOS:2 and 4 (such DNAs are exemplified by the nucleic acid sequences shown in SEQ ID NOS:1 and 3), or variants thereof that encode proteins having at least 85% amino acid sequence homology with a protein according to SEQ ID NO:2 or 4, said protein further retaining the ability to trigger RANK activity when overexpressed in a cell.

Representative examples of expression vectors that can be used to overexpress RANK include, but are not limited to: pDC400 series vectors (Giri et al., EMBO J. 13: 2822–2830 (1994)); pDC300 series vectors; the retroviral vector pBMNZ utilizing the Moloney long terminal repeat (LTR) promoters (Kinsella and Nolan, Human Gene Therapy 7: 1405–1413 (1996)) or retroviral vectors containing a hybrid tetracycline inducible element (pREVTRE) available from Clontech (1020 East Meadow Circle, Palo Alto, Calif. 94303–4230, USA). These same vectors may be used for introducing RANK or RANK-L DNA into cells when introduction of such DNA may be required for other aspects of this invention.

Another method of triggering RANK activity is to express in RANK responsive cells a form of RANK protein which activates one or more RANK-mediated signaling pathways without binding RANK-L, when expressed at normal levels in the RANK responsive cells, such as FEO RANK (SEQ ID NO:10).

In addition to activation of NF-κB, detectable biological responses resulting from RANK triggering include, for example, activation of c-src kinase, activation of JNK, differentiation of osteoclast precursors into osteoclasts, activation of T cells, and so on. C-src is important in proper osteoclast function (see, for example, Lowe et al., Proc Natl Acad Sci USA 90:4485–89 (1993)). In one aspect of the invention, RANK activity is determined by assessing the amount or level of a reporter protein expressed by a promoter/reporter construct in which the reporter gene is operably linked to a RANK-responsive promoter.

As used herein the term "operably linked" refers to nucleic acid sequences that are functionally related to each other, and that preferably are positioned contiguously in a single nucleic acid chain. For example, a regulatory nucleic acid sequence is operably linked to a coding sequence (such as a sequence encoding a reporter protein) if the regulatory nucleic acid sequence controls (either by itself, or in conjunction with one or more other regulatory nucleic acid sequences) the transcription of the coding sequence. Typically, operably linked nucleic acid sequences are contiguous in the same nucleic acid molecule, but in some instances the regulatory sequence may be "trans-acting" and may be present on a different nucleic acid molecule.

Screening Assays for RANK Agonists and Antagonists:

Semi-solid Medium Assays

In one embodiment of the invention, methods are provided that include the steps of: (a) contacting RANK responsive cells with a candidate molecule, the RANK responsive cell being cultured in a semi-solid medium; and (b) observing an enhanced or reduced rate of colony formation by the contacted RANK responsive cell in the semi-solid medium, compared with the rate of colony formation of one or more reference RANK responsive cells that are not contacted with the candidate molecule. When used to screen for a molecule that antagonizes RANK activity, the methods of this aspect of the invention further include the step of stimulating RANK activity in the RANK responsive cell.

As used herein the term "semi-solid medium" refers to a cell growth medium that does not provide a solid substrate to which cells can attach, and that is sufficiently viscous such that cells added to the semi-solid medium are suspended therein, and are thereby prevented from sinking through the semi-solid medium and contacting, and attaching to, the inner surface of the container within which the semi-solid medium is dispensed. Semi-solid media useful in the practice of the present invention typically include a gelatinization agent (such as agar or methylcellulose) dissolved in an aqueous medium in an amount of from 0.1% to 5% (w/v).

In this embodiment of the invention, RANK-responsive cells are plated in a semi-solid medium in the presence of one or more molecules that is to be tested for its ability to modulate RANK activity. The cells used in the practice of this embodiment of the invention express RANK, are capable of forming colonies in a semi-solid medium, and are stimulated by RANK activation to differentiate into cell types that grow slowly in semi-solid medium or that cannot grow in semi-solid medium. The test molecule may be contacted with the cells before or at the time they are plated into the semi-solid medium, or after they have been plated.

In these assays, RANK responsive cells may suspended be in semi-solid medium that is then applied to the surface of a layer of semi-solid medium that includes a higher concentration of gelatinization agent than is present in the semi-solid medium within which the cells are suspended. For example, RANK responsive cells can be suspended in a semi-solid medium that includes agar at a concentration of 0.3% (w/v). The suspended cells can then be plated onto a layer of semi-solid medium that includes agar at a higher concentration, such as a concentration of 0.5% (w/v).

An unusual feature of this semi-solid medium approach for detecting RANK antagonists is that a positive response (that is, colony formation and/or colony growth) is enhanced when an antagonist is present, whereas assays to detect antagonists more typically are designed such that the measured response is abolished in the presence of an antagonist. Moreover, the present assay permits the recovery of cells that are responding to the antagonist, a feature that is particularly useful when the test molecule has been delivered to the cells in the form of a recombinant cDNA library (see below).

Using a semi-solid medium assay, the ability of a test molecule to agonize RANK is detected by contacting RANK-responsive cells with the test molecule, and observing a reduced rate of colony formation or colony growth in semi-solid medium as compared with the rate of colony formation in a reference culture of the same RANK responsive cells that are not contacted with the test molecule. If desired, for detecting RANK agonists, positive control cultures may be used to provide a reference for comparison in which the reference cells are contacted with a known RANK agonist, such as RANK-L or an agonistic anti-RANK antibody.

Cells useful for assays involving semi-solid medium generally include any cells that express RANK, that are capable of forming colonies in a semi-solid medium, and that are stimulated by RANK triggering to differentiate into cell types that cannot form colonies in semi-solid medium. Generally, these cells differentiate into osteoclasts when RANK is triggered. Representative examples of cells useful in the practice of this aspect of the invention include the RAW 264.7 cell line (ATCC Deposit Number TIB-51), undifferentiated hematopoietic cells, which may be obtained from the spleen, peripheral blood or bone marrow cells of any mammalian species, the BCL-X1/Tag cell line which can differentiate into osteoclasts that express TRAP, which generally is considered to be an osteoclast-specific enzyme marker (Hentunen et al., J. Clin. Invest. 102:88–97 (1998)), and the mouse macrophage-like osteoclast progenitor cell line C7 (Nakagawa et al., Biochem. Biophys. Res. Comm. 253:395–400 (1998)). RAW 264.7 cells (a mouse macrophage cell line) are stimulated to differentiate into multinuclear osteoclasts (which cannot form colonies in semi-solid media) by the addition of RANK-L.

Colony formation is assessed by visually comparing the size and/or number of colonies in cultures contacted with a test molecule with the size and/or number of reference colonies present in control cultures of the same RANK responsive cells that have not been contacted with a potential agonist or antagonist of RANK. The size and/or number of colonies is assessed after a desired period of time, such as from 1 to 10 days after contacting the RANK responsive cells with the test molecule, or more preferably, from 5 to 10 days after contacting the cells with the test molecule. Visual comparison of the cultures may be made, for example, using light or phase contrast microscopy.

Again by way of example, the rate of colony formation can be measured within one culture well using changes in visible light transduction as measured spectrophotometrically. In addition, if cells are labeled using a vital fluorescent dye prior to growth in semi-solid media, the rate of colony formation can be assessed fluorometrically. The DNA content of cells in a culture well can also be measured using standard means to assess the rate of colony formation.

If the aforedescribed semi-solid medium approach is used to detect RANK antagonists, the assay will include a step that comprises activating RANK in the cells. The cells are contacted with the test molecule (that is, the putative RANK antagonist) before, during or after the RANK activation step. RANK activation can be accomplished, for example, by overexpressing RANK in the cells, or by contacting the cells with an agonistic anti-RANK antibody or with RANK-L. Alternatively, triggering may be accomplished by co-expressing RANK-L in the RANK-responsive cells, adding RANK-L to the cultures as soluble RANK-L, or it may provided by other means as described herein. If the test molecule is a RANK antagonist, the cells will divide more than in similar cultures to which the test molecule is not added. If a test molecule that is a RANK antagonist is added prior to RANK triggering, more colonies will appear in cultures that are contacted with the test molecule than in cultures that are not contacted with the test molecule. If the antagonist is added after colonies have formed, the colonies exposed to the antagonist will grow larger than colonies in control cultures that were not exposed to the antagonist.

Using the aforedescribed cells, the ability of a test molecule to function as a RANK agonist is detected by contacting the RANK responsive cells with the test molecule, and observing a reduced rate of colony formation in semi-solid medium as compared with the rate of colony formation in a control culture of the same RANK responsive cells that are not contacted with the test molecule. In this assay, a RANK agonist will stimulate the cells to differentiate into a cell type that cannot form colonies in semi-solid media. Cells typically used for these assays will differentiate into osteoclasts when exposed to a test molecule that is a RANK agonist. Control RANK agonists that may be used for these assays include membrane-bound RANK-L and soluble forms of RANK-L.

In one variation of the semi-solid medium assay, this strategy is used to screen a nucleic acid library, such as a cDNA library, that encodes a population of candidate protein molecules that are being screened for their ability to antagonize or agonize RANK activity. The cDNA library is introduced into a population of RANK responsive cells by any art-recognized means, such as by transfection or transduction, as described in more detail below. If RANK antagonists are being sought, cells into which the cDNA molecules have been introduced are cultured in a semi-solid medium, and RANK is triggered in the cells by one of the methods described herein or by another suitable method. The rate of colony formation or the rate of colony growth in the suspended genetically modified cells is compared with that in similar cells into which no DNA other than a control DNA has been introduced. Suitable control cells may receive, for example, vector DNA instead of the cDNA library. Colonies in the genetically modified population which are growing significantly faster than colonies in the control population can be isolated and further studied, The foreign DNA can be retrieved from such colonies to identify and isolate the RANK antagonist that was responsible for a colony's enhanced growth. For example, the introduced nucleic acid molecules can be isolated from the fast growing colonies and the nucleic acid sequence of each can be determined. The protein encoded by the isolated, sequenced, nucleic acid molecule can be expressed and/or chemically synthesized and its ability to antagonize RANK activity confirmed and studied.

Agonists of RANK are recognized in this assay by performing the assay as described above but without triggering RANK; cells containing cDNA encoding a RANK agonist will grow more slowly or will fail to form colonies. cDNA encoding the RANK agonist is recovered from these slow growing as described above.

Many different types of mammalian gene transfer and expression vectors have been developed that are suitable for introducing a cDNA library encoding proteins to be tested in the above semi-solid medium assay for their ability to modulate RANK activity (see, Miller and Calos, eds., "Gene Transfer Vectors for Mammalian Cells," Current Comm. Mol. Biol., Cold Spring Harbor Laboratory, New York, 1987). Naked DNA can be physically introduced into mammalian cells by transfection using any one of a number of techniques including, but not limited to, calcium phosphate transfection (Berman et al., Proc. Natl. Acad. Sci. USA 81: 7176, 1984); DEAE-dextran transfection, protoplast fusion (Deans et al., Proc. Nat'l. Acad. Sci. USA 81: 1292, 1984); electroporation, lipofection (Felgner et al., Proc. Nat'l. Acad. Sic. USA 84: 7413, 1987), polybrene transfection (Kawai and Nishzawa, Mol. Cell. Biol. 4: 1172, 1984) and direct gene transfer by laser micropuncture of cell membranes (Tao et al., *Proc. Natl. Acad. Sc. USA* 84: 4180, 1987).

In addition, various infection techniques have been developed which utilize recombinant infectious, virus particles for gene delivery. The viral vectors which have been used in this manner include virus vectors derived from simian virus 40 (SV40; Karlsson et al., *Proc. Nat'l. Acad. Sc. USA* 82: 158, 1985); adenoviruses (Karlsson et al., *EMBO J* 5: 2377, 1986); adeno-associated virus (LaFace et al., *Virology* 162: 483, 1988) and retroviruses (Coffin, 1985, p17–71 in Weiss et al (eds.), *RNA Tumor Viruses*, 2nd ed., Vol. 2. Cold Spring Harbor Laboratory, New York). These same virus vectors may be used for introducing RANK or RANK-L DNA into cells when introduction of such DNA may be required for other aspects of this invention.

Gene transfer and expression methods are numerous and essentially function to introduce and express genetic material in mammalian cells. Several of the above described techniques have been used to transduce hematopoietic or lymphoid cells, including calcium phosphate transfection (Berman et al., supra, 1984); protoplast fusion (Deans et al., supra 1984); electroporation (Cann et al. *Oncogene* 3: 123, 1988) and infection with recombinant adenovirus (Karlsson et al., supra; Ruether et al. *Mol. Cell Biol.* 6: 123, 1986); adeno-associated virus (LaFace et al., supra); and, retrovirus vector (Overell et al., *Oncogene* 4: 1425, 1989). Primary T lymphocytes have been successfully transduced by electroporation (Cann et al., supra, 1988) and by retroviral infection (Nishihara et al., *Cancer Res* 48: 4730, 1988); Kasid et al., supra, 1990).

Assays involving the aforedescribed semi-solid medium screening strategy are useful as follows for screening collections of molecules, such as libraries of small organic molecules or peptides. Microtiter plates, such as 96-well microtiter plates, may be used, and a different candidate agonist or antagonist of RANK activity is placed in each well together with an aliquot of RANK-responsive cells in semi-solid medium. Cells used for this assay are cells that normally will differentiate and stop dividing in response to RANK triggering (see above for description of suitable cells). If it is desired to detect molecules with RANK antagonist activity, a stimulus for triggering RANK is provided, such as RANK-L, which may be added to the medium or which may be provided by some other means as described herein. Again by way of example, a candidate molecule can be dissolved and distributed throughout the semi-solid medium, or can be applied (in solution form) to the upper surface of the semi-solid medium and allowed to diffuse throughout.

If desired, the nucleic acid molecules introduced into the RANK responsive cells can be stably integrated into the RANK responsive cell genome. For example, a cDNA library constructed in a retroviral vector can be utilized to transfect a RANK responsive cell line. The advantage of stably integrating the introduced DNA molecules into the genome of the RANK responsive cells is that a continuous, high level of gene expression is typically obtained. Example 2 herein discloses a representative protocol for screening for agonists or antagonists of RANK signaling using RAW 264.7 cells and a retroviral expression library.

Another application of the methods of the invention is to screen for molecules (such as cDNAs, proteins and peptides) that complement a defective RANK signal. For example, a form of human RANK (termed "RANKΔ340–421") in which the TRAF6 binding site is missing, cannot stimulate the formation of osteoclasts from hematopoietic precursor cells. This form of RANK is described in Galibert et al., *J. Biol. Chem.* 273:34120, 1998, has an amino acid sequence corresponding to that of human RANK (SEQ ID NO:2) but with the TRAF6 binding site (amino acids 340–421 of SEQ ID NO:2) deleted. The methods of the present invention can therefor be used to screen for molecules that complement the RANKΔ340–421 signaling mutation and thereby permit the formation of osteoclasts from hematopoietic precursor cells. Example 3 herein describes the preparation of RANK responsive cell line that expresses RANKΔ340–421.

Promoter/Reporter Assays Using the MMP-9 or TRAP Promoter

In a further aspect of the invention, provided herein are screening assays that use promoter/reporter constructs that employ promoters that were not previously known to be capable of responding to RANK activation by causing elevated expression of protein coding sequences to which the promoters are operably linked. Specifically, the present promoter/reporter constructs use a promoter derived from a TRAP gene or from a MMP-9 gene. Example 4 herein describes a construct of the murine MMP-9 promoter (Sato et al., J Biol Chem 268:23460–68 (1993); Sato and Seiki, Oncogene 8:395–405 (1993)) fused to the human IL-2α receptor. The human MMP-9 promoter or a TRAP promoter (human or murine; see, for example, Reddy et al., Bone 16:587–593 (1995))also can be used for these screening methods.

Assays according to this aspect of the invention include the steps of: (a) contacting a cultured RANK responsive cell with a test molecule, the RANK responsive cell comprising a nucleic acid molecule encoding a reporter molecule, the nucleic acid molecule encoding a reporter molecule being operably linked to a RANK responsive regulatory nucleic acid sequence; and (b) observing an enhanced or reduced level of expression of the reporter molecule in the contacted RANK responsive cell, compared to the level of expression of the reporter molecule in one or more reference RANK responsive cells that are not contacted with the candidate molecule. When used to screen for a molecule that antagonizes RANK activity, the methods of this aspect of the invention further comprise the step of stimulating RANK activity in the RANK responsive cell.

RANK agonists are identified in this type of assay is detected by observing an increased level of reporter molecule expression in RANK responsive cells contacted with the RANK agonist as compared to the level of reporter molecule expression in control RANK responsive cells that have not been contacted with the RANK agonist, or with any other activator of RANK activity. The control cells are typically the same type of RANK responsive cells as the RANK responsive cells contacted with the RANK agonist. When the assays are directed to identifying RANK agonists, the protocol does not include a RANK triggering step such as deliberately contacting the cells with RANK-L. The presence of a RANK antagonist is detected by observing a reduced level or the absence of reporter molecule expression in RANK responsive cells in which RANK has been triggered and which have been contacted with a candidate antagonist. The level or reporter expression is assessed by comparison with the level of reporter expression in control, RANK responsive cells that have been contacted with a RANK activator, but which have not been contacted with the candidate RANK antagonist. The control cells are typically the same type of RANK responsive cells as the RANK responsive cells contacted with the RANK antagonist.

When this type of assay is used to screen for antagonists of RANK activity, RANK activity must be stimulated in the RANK responsive cells. Typically, RANK activity is triggered before or at the same time as contacting the RANK responsive cells with the candidate molecule(s). In some cases, it may be desirable to stimulate RANK activity after contacting the RANK responsive cells with the candidate molecule. Any procedure that stimulates RANK activity can be utilized, such as those procedures for stimulating RANK activity that are described above.

Cells useful in this aspect of the invention express RANK protein and include at least one signal transduction pathway that is stimulated by the activation of RANK. Some cells useful in this aspect of the invention naturally express RANK and include at least one signal transduction pathway that is stimulated by the activation of RANK. Examples of this type of cell include RAW 264.7 cells, the BCL-X1/Tag osteoclast cell line which can be differentiated into TRAP+ osteoclasts (Hentunen et al., J. Clin. Invest. 102: 88–97 (1998)), and the mouse macrophage-like osteoclast progenitor cell line C7 (Nakagawa et al., Bioch. Biophys. Res. Comm. 253: 395–400 (1998)).

Other cells useful in this aspect of the invention are genetically modified to express RANK and/or to include at least one signal transduction pathway that is stimulated by the activation of RANK. Examples of this latter type of cell include 293/EBNA cells. Virtually any cell type capable of growth in culture may be genetically modified to express RANK for the purposes of these assays. Numerous other suitable methods for introducing RANK DNA into a cell are described elsewhere in this disclosure, and include viral vectors and other methods such as electroporation, lipofection and so on.

The RANK-responsive cells can be contacted with one or more candidate molecules in any acceptable manner, such as by utilizing those procedures that are described above or by any other desired method.

Reporter molecules that are useful in this embodiment of the invention include luciferase, β-galactosidase, green fluorescent protein, alkaline phosphatase and any heterologous surface protein which can be detected on the surface of a RANK responsive cell, such as by using a specific antibody directed against the heterologous protein. Examples of useful heterologous surface proteins include the human IL-2 receptor, the murine IL-4 receptor (abbreviated as mIL-4R), the human CD2, CD4 or CD8 proteins.

Assays Based on Detecting c-src Activity or F-actin Rings

In another aspect of the invention, assays are provided for screening for a molecule RANK and RANK-L antagonists by measuring the extent to which a candidate molecule enhances or inhibits the RANK-mediated induction of c-src tyrosine kinase activity and/or F-actin ring formation. F-actin rings are cytoskeletal structures that are characteristic of active osteoclasts (Lakkakorpi and Vaananen, J. Bone Min. Res. 6:817–26 (1991)).

To detect F-actin rings, cells are fixed, such as by exposure to 3% paraformaldehyde, and visualized by staining cells with a fluorescent probe that binds specifically with actin. A suitable fluorescent tag is phalloidin, which can be obtained from Molecular Probes, Eugene, Oreg. The fluorescent signal is detected, for example, using a standard fluorescent microscope, and the number of cells having F-actin rings is visually quantified. An F-actin ring is identified as a continuous ring of F-actin at the periphery of a cell, and these distinct structures are visible through a microscope. F-actin rings do not appear in cell types other than osteoclasts.

To detect c-src activity, phosphotransferase activity of this enzyme is measured using a synthetic substrate, such as the p34/cdc2 peptide (KVEKIGEGTYGVVYK) (SEQ ID NO:13), which functions as a substrate for the enzyme. An exemplary assay for measuring c-src activity is provided in Example 8.

This aspect of the invention utilizes cells that express a RANK protein that is capable of activating the cells to differentiate into osteoclasts, or any cells that respond to RANK triggering by activating c-src activity. In a preferred embodiment of this aspect of the invention, the RANK protein induces elevated levels of c-src tyrosine kinase activity and F-actin ring formation while the cells are undergoing differentiation. Exemplary cells useful in this embodiment are any cells that are capable of differentiating into osteoclasts in response to RANK triggering and that also express a form of RANK that is capable of inducing c-src activity and F-actin ring formation. Such cells include primary hematopoietic cells that have been enriched for osteoclast precursors, or a cell line such as RAW 264.7 cells. Suitable primary hematopoietic precursors can be derived from bone marrow cells, fetal liver or peripheral blood. Suitable cells also include cells that have been genetically modified to express RANK, using the methods described above.

For this type of assay, the test molecule may be added to the culture medium for up to about five days after differentiation is complete. C-src activity or F-actin ring formation is assayed after the cells have been exposed to the test molecule for any convenient time period. For example, the activity is measured after 6 to 12 hours, after one day, after two days, after three days, after four days, after five days or after a longer period of exposure. A test molecule is identified as being a RANK agonist if after exposure to the test molecule the amount of F-actin rings or c-src activity detected in the cells is increased as compared with the level observed in control RANK−/−cells into which no RANK DNA was introduced.

In this type of assay, test molecules also may be evaluated for their ability to complement certain biological activities that are characteristic of the wild-type RANK protein. Generally, this type of assay exploits the fact that wild-type RANK protein can induce c-src activity and F-actin ring formation in cells that are undergoing the process of differentiating into osteoclasts. However, these two activities of RANK can be abrogated by deleting the TRAF6 binding domain from the RANK protein (see Example 8), although the TRAF6 binding domain is not required in order for RANK activation to be able to induce osteoclast differentiation. Thus, when TRAF6 deletion mutants of the RANK protein are expressed in osteoclast precursors, triggering RANK will cause the cells to differentiate, but will not cause them to express higher levels of c-src activity nor will these cells exhibit F-actin rings. For human RANK protein, the TRAF6 binding domain is encompassed within a region defined by amino acids 340–421 of SEQ ID NO:2. Thus, cells in which such RANK mutants are expressed can be used in assays to screen for molecules capable of complementing the TRAF6 binding site deletion in the mutant RANK. The ability of a test molecule to complement this defect is detected by observing that when the test molecule is contacted with cells expressing the RANK mutant, c-src activation and F-actin formation do occur when RANK is triggered.

Cells suitable for use with TRAF6 mutants of RANK include primary hematopoietic precursor cells from RANK knock-out animals, such as the previously described RANK−/−mice (Dougall et al., 1999). To perform this assay, cells from a RANK knock-out animal are genetically modified by introducing a DNA encoding a mutant RANK protein that lacks a TRAF6 binding region. Exemplary DNAs for this purpose are mouse or human RANK DNA from which the TRAF6 binding domain coding sequences have been deleted. Suitable means for introducing the RANK DNA include infection with a viral vector (such as a retroviral or adenovirus vector) into which the DNA encoding the protein has been ligated, or any of the other means discussed above. After introducing the RANK mutant DNA, the cells are induced to differentiate into osteoclasts by triggering the RANK protein using any of the means of RANK triggering that are described above or any other desired means of triggering RANK. To determine if a test molecule complements the defect in this mutant form of RANK, the molecule is added to the culture medium for part or all of the incubation period during which the cells are undergoing differentiation.

Screening Assays Involving $CaPO_4$ Resorption

Provided also are methods of screening for RANK agonists or antagonists in assays based on the RANK-dependent resorption of a synthetic matrix of calcium phosphate. Wild-type RANK protein can enable cells to differentiate into osteoclasts that are capable of resorbing calcium phosphate ($CaPO_4$), while signals from a RANK protein lacking a TRAF6 binding site do not initiate $CaPO_4$ resorption. Cells useful for this screening assay include any cells in which the activation of RANK leads to $CaPO_4$ resorption, that is, cells that differentiate into osteoclasts when RANK is triggered. Exemplary cells for use in this assay include primary hematopoietic precursors, primary hematopoietic cells, RAW 264.7 cells, or any cell transfected with a form of RANK that supports this activity (such as osteoclast precursor cells from RANK−/−mice).

In one embodiment of the invention, this method is used to screen for molecules that complement inactive RANK mutants, such as the TRAF6 deletion mutants as described above.

Suitable procedures for performing this assay are exemplified by those set forth in Example 9. Generally, cells are cultured on commercially available thin microscope slides that are thinly coated with $CaPO_4$ RANK responsive cells so grown will respond to RANK triggering by differentiating into cells that resorb $CaPO_4$, resulting in the formation of a discrete pit in the $CaPO_4$ film. To detect a RANK antagonist, the number of pits on slides contacted with the test molecule is compared with the number of pits on slides not contacted with the test molecule.

RANK agonists are detected in this type of assay by growing suitable cells on $CaPO_4$ films and contacting the cells with a test molecule without first triggering RANK in the cells.

The following examples illustrate the best mode now contemplated for practicing the invention, but should not be construed to limit the invention.

EXAMPLE 1

This example describes evaluating murine 3T3 cells transfected with plasmids containing DNA encoding human FEO RANK (SEQ ID NO:9), and murine 3T3 cells expressing recombinant DNA encoding human wild type RANK (SEQ ID NO:1) for their relative ability to activate endogenous c-jun kinase (JNK) in the absence of RANK-L stimulation. JNK is known to be activated as a consequence of RANK signal transduction.

For JNK assays, whole cell extracts were prepared from 3T3 cells 24 hours after transfection. Cells were lysed in a buffer containing 20 mM HEPES, pH 7.4, 2 mM EGTA, 50 mM β-glycerol phosphate, 1 mM DTT, 1 mM sodium orthovanadate, 1% Triton-X 100, 10% glycerol and the protease inhibitors leupeptin, pepstatin A, and PMSF. Clarified lysates were immunoprecipitated with 1 µg each anti-JNK (FL) and anti-JNK (C17) antibodies (both from Santa Cruz Biotechnology, Inc. Santa Cruz, Calif.). The immune complexes were washed three times in lysis buffer, two times with wash buffer (500 mM LiCl, 100 mM Tris, pH 7.5, 0.1% Triton X-100, 1 mM DTT) and three times in assay buffer (20 mM MOPS, pH 7.0, 2 mM EGTA, 10 MM $MgCl_2$, 1 mM DTT, 0.1% Triton X-100). JNK activity was determined by an immune-complex assay using 1 µg of a fusion protein of glutathione-S-transferase and amino acids 1–169 of c-jun kinase (GST-cJun (1–169)) (UBI, Lake Placid, N.Y.) and 5 µCi of [$^{32}$P]-ATP as substrate in 40 µl of assay buffer at 30° C. for 20 min. Reaction products were resolved on 4–20% SDS/PAGE and visualized by autoradiography.

JNK was activated in response to expression of FEO RANK, but not in response to expression of wild type RANK.

EXAMPLE 2

This example describes screening for antagonists of RANK signaling using RAW 264.7 cells and a retroviral expression library in a semi-solid medium assay.

A retroviral cDNA library is constructed in pBMNZ. Preferably the cDNA is synthesized against mRNA isolated from cells that do not form osteoclasts, i.e., cells that may express antagonists of RANK activity (e.g., macrophages activated with GM-CSF or IL-10). Retroviral particles are packaged using the Phoenix cell lines (provided by Dr. Gary Nolan, Stanford University, USA) and appropriate envelope protein (such as ecotropic envelope protein, amphotropic envelope protein or polytropic envelope protein). For example, in the case of transiently produced retroviral vectors, Phoenix packaging cells are transfected with constructs generated in the pBMNZ retroviral vector, and the culture supernatant is harvested 48 hrs post-transfection. The retroviral particles are isolated using standard techniques. For example, viral particles are purified from membrane fragments by sterile filtration through a 0.45 micron filter.

RAW 264.7 cells are infected with the packaged retroviral cDNA library under conditions which lead to optimal infection. For example, optimal infection conditions can be determined by monitoring the expression of a reporter gene expressed from a test retroviral construct. Retroviral constructs encoding β-galactosidase (e.g., pBMNZ/LZRS; Kinsella and Nolan, 1996, supra) can be used to produce retroviral particles. After infection of cells with a serial dilution of the virus stocks, the number of β-galactosidase expressing cells can be monitored 24 hr after infection. Various conditions including the choice of envelope protein, multiplicity of infection, length of infection incubation time, pre-treatment of cells under conditions to promote cell-cycling, co-factors such as polybrene or recombinant fibronectin fragments can be varied in order to determine the conditions under which the largest amount of test virus enters the cells.

Cells are then plated in a semi-solid medium after the appropriate time allowing for expression of cDNAs in the infected cells. Exemplary conditions for plating infected cells are plating, in each well of a 24-well plate, 3 ml of 0.3% (w/v) methylcellulose medium containing infected cells at a cell density of from $1\times10^5$ cells/ml to $1\times10^6$ cells/ml. A soluble leucine zipper form of RANK-L (200 ng/ml) is included in the semi-solid medium.

Cells are cultured for a period of from 5 days and 8 days and colonies derived from the infected cell population that are growing significantly faster than the colonies derived from the uninfected, control population are isolated for further analysis. For example, the colonies of interest are aseptically isolated and grown further in the absence of RANK activation in order to increase the cell numbers. The cDNA clone within the cells of each colony is recovered by any art-recognized technique, such as RT-PCR of the expressed viral transgene, PCR of the incorporated provirus or via a helper viral recombination and recovery of viral particles. For example, amplification of integrated cDNAs has been described by Kitamura et al., Proc. Natl. Acad. Sci. USA 92: 9146–9150 (1995).

A variation of this assay takes advantage of the cell-fusion and terminal differentiation that occurs when RAW264.7 cells are contacted with RANK-L. To perform this variation of the assay, RAW264.7 cells are plated in a 6 well culture plate, a soluble leucine zipper form of RANK-L is added to the wells, and the plates are incubated for 3 to 5 days in the presence of the leucine zipper RANK-L polypeptide. Cells that respond positively to the RANKL trigger will fuse into large multinuclear differentiated osteoclasts and will lose their potential to divide in culture. If desired, other forms of RANKL besides leucine zipper RANKL can be used as the stimulus in this assay. To use this assay to test various agents for their capacity to antagonize RANK, the putative antagonist is added to the wells prior to and/or during exposure to the RANKL stimulus. If a candidate antagonist, such as an expressed cDNA, abrogates the cells' responsiveness to RANK-L, the cells will retain their capacity to divide in these cultures. Cells from these plates that remain capable of growth in culture can be separated and recovered from the fused differentiated osteoclasts by vigorous pipetting or by trypsin digestion. These recovered cells will be able to grow in normal growth media in the absence of RANKL, thus they can be enumerated and propagated using conventional techniques. As described above, the cDNAs within the propagated cells are recovered by conventional techniques, such as reverse-transcriptase PCR of the expressed viral transgene, PCR of the incorporated provirus or via a helper viral recombination and recovery of viral particles.

EXAMPLE 3

This example describes the preparation of RANK responsive cell line that expresses RANKΔ340–421 (see Galibert et al., 1998 for description of RANKΔ40–421).

Spleen cells were isolated from 3–6 week old RANK–/– mice (which have a defect in osteoclast formation and are osteopetrotic) and lineage depleted in the following manner. T-cells were removed by immunoabsorption using biotinylated anti-CD3 antibodies; erythroid cells were removed by immunoabsorption using biotinylated anti-Ter-119 antibodies; and granulocytes were removed by immunoabsorption using biotinylated anti-GR-1 antibodies. The antibody-cell complexes were removed by binding the biotin moiety to streptavidin-conjugated magnetic beads, which were then passed over a metallic MACS depletion column.

The lineage depleted cells were then incubated for 48 hrs in 40 ng/ml CSF-1 and infected using retroviral supernatants (MOI of 5) in the presence of recombinant fibronectin fragments (Retronectin, PanVera Corp, Madison, Wis.) for an additional 48 hr in 40 ng/ml CSF-1. Following infection, spleen cells were harvested and plated in MEM 10% FBS containing 40 ng/ml CSF-1 and 200 ng/ml murine RANK-L. Cells were then cultured under these conditions for 5 days to allow differentiation of osteoclasts.

The retroviruses used for transfection were prepared by subcloning DNA encoding RANKΔ340–421 into the pBMNZ vector (Kinsella and Nolan, 1996, Human Gene Therapy 7:1405–1413). The entire RANKΔ340–421 cDNA was excised from pDC304/RANKΔ340–421 (Galibert et al., J. Biol. Chem. 273:34120, 1998) using the restriction endonucleases Bgl II and Not I. This cDNA insert fragment was ligated into the retroviral vector pBMNZ (Kinsella and Nolan, 1996, supra) that had been digested with Bam HI and Not I. The resultant plasmid was purified, the DNA sequence confirmed and designated pBMNZ/RANKΔ340–421. Production of infectious retroviral vector particles in 293-E Phoenix packaging cells was performed as described (Kinsella and Nolan, 1996, supra).

EXAMPLE 4

This example describes the preparation of promoter/reporter vectors of the murine MMP-9 promoter (SEQ ID NO:11) fused to the human IL-2α receptor.

A DNA fragment containing the promoter region of the murine MMP-9 gene was fused to a cDNA molecule encoding the human IL-2α receptor as follows. A plasmid containing 4.15 kb of the murine MMP-9 promoter region (SEQ ID NO:11) was subcloned into the promoter deficient pGL2 basic vector (Promega, Madison, Wis.) containing the luciferase reporter gene as described by Roach et al., Gene 208: 117–122 (1998). The resultant plasmid was designated pGB-colNK1. An approximately 3.5 kb Sma I/EcoRI fragment containing the MMP-9 5' flanking promoter sequence (SEQ ID NO:11) was excised from pGB-colNK1 and subcloned into the SIN retroviral vector pSIR (Clontech) at the Barn HI site which had been made blunt-ended.

A cDNA encoding the human IL-2α receptor was subcloned into CAVNOT as described in Cosman, D., et al. "Cloning and expression of human and mouse 1L-2 receptor cDNAs". In: Lymphokines: Molecular Cloning and Analysis of Lymphokines. D. R. Webb and D. V. Goeddel (eds.) Academic Press, 1987, p. 109.

The human IL-2α receptor cDNA was amplified from the CAVNOT construct using PCR such that the 5' end was modified to include a Bgl II site and the 3' end was modified to include a PflM1 site. This amplified product was ligated into the pGEM-T vector (Promega). The human IL-2α receptor cDNA was excised from this plasmid using Bgl II and PflM1 restriction sites and ligated into pGL2 basic (Promega) which had been digested with Bgl II and PflM1 to excise the luciferase reporter cDNA. The human IL-2α receptor thus replaced the luciferase reporter in pGL2, and the resulting plasmid was designated pGL2/hIL-2 receptor.

The pGL2/hIL-2 receptor was digested with KpnI and Bgl II within the polylinker upstream of the cDNA encoding human IL-2α receptor. A 3.5 kb Kpn I/NheI fragment isolated from the pGB-colNK1 plasmid encoding the MMP-9 promoter (SEQ ID NO:11) and the contiguous Nhe I to Bgl II (653 bp) fragment of the remaining MMP-9 promoter were ligated in a trimolecular ligation with the pGL2/hIL-2 receptor forming the plasmid termed pGL2-MMP-9/human IL-2 receptor in which the entire 4.15 kb 5' flanking sequence of the mouse MMP-9 flanking region is fused directly upstream of the hIL-2α receptor cDNA. This construct exhibited responsiveness to RANK.

In order to test the inhibitory activity of a candidate molecule using this system, the candidate molecule may be added prior to, simultaneous with or after addition of the RANK activity agonist. The level of IL-2α receptor expression on the surface is a measure of the level of RANK activation.

The location of the RANK-responsive portion of MMP-9 promoter was more narrowly identified by testing further truncations of the promoter. A PVUII/BGL2 restriction fragment including the 5'-proximal 1822 bp of the MMP-9 promoter was fused with a BLGII/EcoRI restriction fragment encoding the human IL-2 receptor α in the multicloning site of the pSIR retroviral vector (Clontech). The resulting plasmid, which was named pSIR/MMP-9, is responsive to RANK and is useful in assays to identify RANK antagonists. The region of the MMP-9 promoter present in pSIR/MMP-9 corresponds to nucleotides 1769–3591 of SEQ ID NO:11.

pSIR/MMP-9 was introduced into RANK responsive cells as follows. Retroviral particles were prepared after transfection of 293/E packaging cells with pSIR/MMP-9. RAW264.7 cells were infected with these particles and neomycin resistant colonies stably expressing the reporter were isolated. Treatment of these cells with RANKL led to an increase in the cell surface expression of the hIL-2 αR, as detected by flow cytometry using the mouse mAb (clone 2A3) anti-human IL-2 αR as a reagent for detecting the IL-2R. Expression of hIL-2α receptor was observed within 4 hours and reached the maximal level observed within 48 hr.

Surface expression of human IL-2α receptor is detected by flow cytometry in the following manner. Cells are harvested and known, specific, antibody binding sites are blocked using a solution of PBS containing 5% normal goat serum for 30 minutes at 4° C. Cells are then washed and incubated with the anti-human IL-2α receptor monoclonal antibody clone, at an antibody concentration of 5 μg/ml for 1 hour at 4° C. Following this incubation, cells are washed and a fluorescently conjugated, anti-mouse IgG secondary antibody is incubated with the cells for an additional thirty minutes at 4° C. After washing the cells, the fluorescence intensity is measured using a flow cytometer, such as a FACS scan (Becton Dickinson).

Additionally, surface expression of human IL-2α receptor can be analyzed using a radioactive antibody against IL-2α receptor. For the mIL-4R-specific radioimmune assay, mouse anti-human IL-2α monoclonal antibody reactive with mIL-4R was labeled with $^{125}$I via a Chloramine T conjugation method; the resulting specific activity is typically 1.5× $10^{16}$ cpm/nmol. After 48 hours, cells transfected with pGL2-MMP-9/human IL-2 receptor were washed once with media (DMEM, 12 5% FBS). Non-specific binding sites were blocked by the addition of pre-warmed binding media containing 5% non-fat dry milk and incubation at 37° C./5% $CO_2$ in a tissue culture incubator for one hour. The blocking media was decanted and binding buffer containing $^{125}$I anti-mIL-4R (clone M1; rat IgG1) was added to the cells and incubated with rocking at room temperature for 1 hour. After incubation of the cells with the radio-labeled antibody, cells were washed extensively with binding buffer (2x) and twice with phosphate-buffered saline (PBS). Cells were lysed in 1 ml of 0.5M NaOH, and total radioactivity measured with a gamma counter. Using this assay, 293/EBNA co-transfected with DNAs encoding RANK demonstrated transcriptional activation, as shown by detection of muIL-4R on the cell surface. Overexpression of RANK resulted in transcription of muIL-4R, as did triggering of the RANK by RANK-L. Similar results are observed when RANK is triggered by agonistic antibodies.

Further, cells expressing human IL-2α receptor on their surface can be isolated using a panning technique, such as the technique described by Aruffo and Seep, PNAS 84:8573–8577 (1987). In brief, a secondary antibody which recognizes the primary antibody is immobilized onto bacteriological 60 millimeter plates. The cells to be panned are prepared as single cell suspensions in PBS containing 0.5 mM EDTA and 5% FBS. The antibody to the cell-surface marker is added at approximately 5 μg/ml followed by incubation on ice for 30 minutes. Cells are washed once and added to the second antibody-coated plates in PBS/EDTA/5% FBS, and incubated at room temperature for 1–3 hours. Excess cells not adhering to the dish are removed by gentle washing with PBS/5% FBS.

EXAMPLE 5

This example describes the activation of the TRAP promoter. A 2.6 kb DNA fragment containing the human TRAP promoter was obtained by digesting the plasmid pBL2HT2.2 with the restriction endonuclease ApaI. The cloning of the human TRAP gene 5' region and the construction of pBL2HT2.2 are fully described in Reddy et al. (Bone 16:587–593 (1995)). A DNA containing the mouse TRAP promoter (SEQ ID NO:12) and a DNA containing the murine MMP-9 promoter (SEQ ID NO:11) also were used for these experiments. DNAs containing the promoters were fused to the luciferase reporter gene. These promoter/reporter constructs were transfected into human 293/EBNA cells along with various combinations of expression vectors that encoded full-length human RANK (SEQ ID NO:2) and human full-length RANK-L proteins (SEQ ID NO:6).

For the mouse TRAP promoter (SEQ ID NO:12), 2×10$^5$ 293/EBNA cells were transfected using DEAE/dextran with 40 ng of a plasmid encoding approximately 2 kb of the mouse TRAP promoter (SEQ ID NO:12) fused to a luciferase reporter, 20 ng of an expression vector encoding RANK-L (SEQ ID NO:6), and 0.4 ng of an expression vector encoding RANK (SEQ ID NO:2). Twenty four hours after transfection, luciferase activity in cell lysates was measured according to manufacturer's instructions (Promega) using a EG&G/Berthold luminometer. Expression of RANK was sufficient to increase reporter expression (approximately 2-fold) while the combination of RANK (SEQ ID NO:2) and RANK-L (SEQ ID NO:6) increased reporter expression approximately 4-fold.

For the human TRAP promoter, the 1.9 kb ApaII fragment containing the promoter activity isolated from the region upstream of the human TRAP gene (Reddy et al., 1995) was fused to a luciferase reporter and transfected (40 ng) into 293/EBNA cells. The combination of human RANK (SEQ ID NO:2) and human RANK-L (SEQ ID NO:6) increased reporter expression approximately 1.5 fold.

For the murine MMP-9 promoter experiments, 4.1 kb of the murine MMP-9 promoter (SEQ ID NO:11) were fused to a luciferase gene and transfected (40 ng) into 293/EBNA cells. Transfection of either RANK (SEQ ID NO:2) alone or the combination of RANK (SEQ ID NO:2) plus RANK-L (SEQ ID NO:6) increased reporter expression 2.5-fold.

Additionally, RAW 264.7 cells (6×10$^6$ cells) were transfected with 15 μg of MMP-9(SEQ ID NO:11)/luciferase plasmid DNA using DEAE/dextran. Two hours after transfection, cells were divided into two equal amounts and further incubated for 24 hours. Addition of 1 μg/ml of a leucine zipper form of murine RANK-L for 18 hours was sufficient to induce the MMP-9(SEQ ID NO:11)/luciferase promoter 10–15 fold.

Quantitative RT-PCR measurements of mouse TRAP and mouse MMP-9 mRNA in RAW 264.7 cells after treatment with either mouse RANKL/LZ (200 ng/ml) or TNFα (20 ng/ml) for various times revealed that TRAP mRNA is elevated greater than 250-fold by RANK-L, but is only increased by about 2.3-fold by TNFα. MMP-9 mRNA is elevated greater than 350-fold by RANK-L, but is not increased by TNFA. This specificity is helpful in screening for inhibitors of RANK signal transduction.

EXAMPLE 6

This example illustrates the preparation of monoclonal antibodies against RANK-L. Preparations of purified recombinant RANK-L, for example, or transfixed cells expressing high levels of RANK-L, are employed to generate monoclonal antibodies against RANK-L using conventional techniques, such as those disclosed in U.S. Pat. No. 4,411, 993, incorporated herein by reference. DNA encoding RANK-L can also be used as an immunogen, for example, as reviewed by Pardoll and Beckerleg in Immunity 3: 165, 1995. Such antibodies are likely to be useful in interfering with RANK-L signaling (antagonistic or blocking antibodies), as components of diagnostic or research assays for RANK-L or RANK-L activity, or in affinity purification of RANK-L.

To immunize rodents, RANK-L immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. DNA may be given intradermally (Raz et al., Proc. Natl. Acad. Sci. USA 91: 9519, 1994) or intramuscularly (Wang et al., Proc. Natl. Acad. Sci. USA 90: 4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with RANK-L, for example, by adaptations of the techniques disclosed by Engvall et al., Immunochem. 8: 871 (1971) and in U.S. Pat. No. 4,703,004. A preferred screening technique is the antibody capture technique described by Beckman et al., J. Immunol. 144: 4212 (1990). Positive clones are then injected into the peritoneal cavities of syngeneic rodents to produce ascites containing high concentrations (>1 mg/ml) of anti-RANK-L monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANK-L protein. Using the methods described herein to monitor the activity of the mAbs, both blocking (i.e., antibodies that bind RANK-L and inhibit binding to RANK) and non-blocking (i.e., antibodies that bind RANK-L and do not inhibit binding) are isolated.

EXAMPLE 7

This example illustrates the preparation of monoclonal antibodies against RANK. Preparations of purified recombinant RANK, for example, or transfected cells expressing high levels of RANK, are employed to generate monoclonal antibodies against RANK using conventional techniques, such as those disclosed in U.S. Pat. No. 4,411,993. DNA encoding RANK can also be used as an immunogen, for example, as reviewed by Pardoll and Beckerleg in Immunity 3: 165, 1995.

To immunize rodents, RANK immunogen is emulsified in an adjuvant (such as complete or incomplete Freund's adjuvant, alum, or another adjuvant, such as Ribi adjuvant R700 (Ribi, Hamilton, Mont.), and injected in amounts ranging from 10–100 μg subcutaneously into a selected rodent, for example, BALB/c mice or Lewis rats. DNA may be given intradermally (Raz et al., Proc. Natl. Acad. Sci. USA 91: 9519, 1994) or intramuscularly (Wang et al., Proc. Natl. Acad. Sci. USA 90: 4156, 1993); saline has been found to be a suitable diluent for DNA-based antigens. Ten days to three weeks days later, the immunized animals are boosted with additional immunogen and periodically boosted thereafter on a weekly, biweekly or every third week immunization schedule.

Serum samples are periodically taken by retro-orbital bleeding or tail-tip excision for testing by dot-blot assay (antibody sandwich), ELISA (enzyme-linked immunosorbent assay), immunoprecipitation, or other suitable assays, including FACS analysis. Following detection of an appropriate antibody titer, positive animals are given an intravenous injection of antigen in saline. Three to four days later, the animals are sacrificed, splenocytes harvested, and fused to a murine myeloma cell line (e.g., NS1 or preferably Ag 8.653 [ATCC CRL 1580]). Hybridoma cell lines generated by this procedure are plated in multiple microtiter plates in a selective medium (for example, one containing hypoxanthine, aminopterin, and thymidine, or HAT) to inhibit proliferation of non-fused cells, myeloma-myeloma hybrids, and splenocyte-splenocyte hybrids.

Hybridoma clones thus generated can be screened by ELISA for reactivity with RANK, for example, by adaptations of the techniques disclosed by Engvall et al., Immunochem. 8: 871 (1971) and in U.S. Pat. No. 4,703,004. A preferred screening technique is the antibody capture technique described by Beckman et al., J. Immunol. 144: 4212 (1990). Positive clones are then injected into the peritoneal cavities of syngeneic rodents to produce ascites containing high concentrations (>1 mg/ml) of anti-RANK monoclonal antibody. The resulting monoclonal antibody can be purified by ammonium sulfate precipitation followed by gel exclusion chromatography. Alternatively, affinity chromatography based upon binding of antibody to protein A or protein G can also be used, as can affinity chromatography based upon binding to RANK protein.

Monoclonal antibodies were generated using RANK/Fc fusion protein as the immunogen. These reagents were screened to confirm reactivity against the RANK protein. Using the methods described herein to monitor the activity of the mAbs, both blocking (i.e., antibodies that bind RANK and inhibit binding of a ligand to RANK) and non-blocking (i.e., antibodies that bind RANK and do not inhibit ligand binding) were isolated.

EXAMPLE 8

In this assay, test molecules capable of modulating an activity associated with RANK are identified by measuring the induction of c-src tyrosine kinase or F-actin ring formation in the presence of the test molecule.

Experiments were conducted in which DNA encoding wild-type or human RANK/TRAF6 binding mutant (RANK α340–421) was introduced into hematopoietic cells isolated from RANK−/−mice. Full-length and mutant human RANK DNAs were subcloned into the pBMNZ retroviral vector as previously described (Kinsella and Nolan, 1996, *Human Gene Therapy* 7:1405–1413). Infectious RANK-containing retrovirus was produced in 293-E Phoenix packaging cells as described (Kinsella and Nolan, 1996). Supernatants from these cells were used as a source of infectious virus particles.

The generation of the RANK−/−mice used in these assays has been described previously (Dougall et al., 1999). Spleen cells were isolated from 3–6 week old RANK−/−mice and enriched for osteoclast precursors by depleting the initial cell population of various types of cells other than osteoclast precursors. For this "depletion" step, the cells were incubated with biotinylated antibodies against CD3 (specific for T cells), Ter-119 (specific for erythrocytes), and GR-1 (specific for granulocytes). After the antibodies had bound to their respective target cells, streptavidin-conjugated magnetic beads were added to the culture, and the mixture of cells was passed over magnetic columns (MACS depletion columns; MILLTENNYI). Cells that did not adhere to the MACS columns were considered to be enriched for osteoclast precursors and were used for the assays.

Cells enriched for osteoclast precursors were incubated for 48 hrs in 40 ng/ml CSF-1 prior to being infected with retroviral supernatants (MOI of 5) in the presence of recombinant fibronectin fragments (Retronectin, PanVera Corp, Madison, Wis.) for an additional 48 hr in 40 ng/ml CSF-1. Both the cells and the virus particles tend to adhere to fibronectin, thus the fibronectin fragments served to enhance the rate of infection by creating a localized high concentration of both cells and virus. Following infection, the cells were harvested and plated in a-MEM 10% fetal bovine serum containing 40 ng/ml CSF-1 and 200 ng/ml MRANK-L and were incubated for 5 days in this medium.

For infected cultures that received wild-type RANK DNA, c-src levels were fairly high following differentiation. In a typical experiment, extracts from cells expressing wild-type RANK wall incorporate about 15-fold more $^{32}$p into a c-src-specific substrate than extracts from cells that are defective in RANK. Both fetal bovine serum and CSF-1 contribute to the basal level of c-src activity, thus this basal level was reduced by "starving" the cells for 18 hrs in MEM containing 0.5% instead of 10% fetal bovine serum and 10 ng/ml instead of 40 ng/ml CSF-1, followed by 2 hours in MEM containing 0.5% FBS and no CSF-1.

To induce c-src and F-actin rings, recombinant mRANK-L/leucine zipper protein was added to the cultures at a concentration of 1 μg/ml for various times after which the cells were lysed in a buffer containing 50 mM HEPES (pH 7.2), 10% glycerol, 250 mM NaCl and 1% Triton X-100. The c-src protein was purified by immunoprecipitation using the monoclonal antibody GD-1. C-src activity in the immune complex was monitored using a commercially available assay kit (Upstate Biotechnology, Lake Placid, N.Y.). In brief, the measurement of c-src activity entailed measuring the phosphotransferase activity using γ-labeled ATP and the p34/cdc2 peptide (KVEKIGEGTYGVVYK) (SEQ ID NO:13), which provides a substrate for the c-src kinase. The kinase assays were incubated at 30° C. for 10 minutes in a buffer containing 10 μCi of gamma-labeled ATP, MnCl$_2$ (75 mM), ATP (500 μM), MOPS (20 mM), beta-glycerol phosphate (25 mM), EGTA (5 mM), sodium orthovanadate (1 mM), and dithiothrietol (1 mM). The phosphorylated substrate peptide was then separated from the residual labeled ATP using phosphocellulose paper and labeled peptide was quantified using a scintillation counter. The immunoprecipitation and in vitro immune complex kinase assay were performed as described (Musch, et al. *J. Biol. Chem.* (1999) 274:7923–7928).

When c-src induction was assayed as described above, it was observed that when cells were induced to differentiate after the introduction of a full-length RANK transgene, the cells contained high levels of c-src activity. In contrast, c-src activity was not discernibly different from background levels in extracts of cells differentiated after infection with either a control virus (encoding lacZ) or with RANK DNA lacking the TRAF6 binding domain (RANK Δ340–421). Background levels were determined using RANK−/−cells that were not infected with retrovirus.

A procedure to detect F-actin rings was carried out as follows. Primary hematopoietic cells from the RANK−/− mice were infected with retroviral constructs encoding either the full-length human RANK cDNA or the RANK/TRAF6 binding mutant (RANK Δ340–421). Cells were cultured on LabTek Chamber slides with #1 borosilicate coverglasses (Nalge/Nunc). After incubation for 5 days in MEM containing 10% fetal bovine serum containing 40 ng/ml CSF-1 and 200 ng/ml mRANK-L. The media was aspirated, washed twice in PBS and then fixed in a solution of 3% paraformaldehyde for 10 minutes, followed by quenching in 50 mM NH$_4$Cl. The F-actin rings were visualized by staining the cells with a fluorescent probe for actin, phalloidin (Molecular Probes, Eugene, Oreg.). The fluorescent signal was detected using a standard fluorescent microscope, and F-actin rings were identified as continuous rings of F-actin at the periphery of individual cells.

F-actin rings were visualized in the cells by staining with fluorescent phalloidin. For cells infected with wild-type RANK DNA, F-actin rings were detected in more than 50% of the cells. However, when the cells had been transfected with the human RANK/TRAF6 binding mutant, all of the cells had a disorganized F-actin cytoskeletal structure and no F-actin rings were discerned.

To assay for an agonist of RANK activity, a test molecule is added to the culture medium during the RANK-L exposure step, or after the differentiation step is completed. If the test molecule is an agonist of RANK activity, cells infected with the above-described deletion mutant will express F-actin rings or will express detectable c-src activity or both. However, RANK agonists that require the presence of a TRAF6 binding site in the RANK molecule will not test positive in RANK−/−cells infected with a RANK TRAF6 deletion mutant.

EXAMPLE 9

The resorption of CaPO$_4$, upon which this assay is based, is considered to be a measure of osteoclast activity. Spleen cells were isolated from 3–6 week old RANK−/−mice and treated as described in Example 9 to remove cells expressing the CD3, Ter-119, and GR-1 antigens. Cells not expressing any of these antigens were harvested and infected as described in Example 9 with retroviral vector particles containing full-length or TRAF6 binding site deletion mutants of RANK.

Following infection, the spleen cells were harvested and plated in MEM containing 10% fetal bovine serum containing 40 ng/ml CSF-1 and 200 ng/ml mRANK-L onto 16 well quartz slides coated with a thin film of $CaPO_4$ (Osteologic, BD Biosystems). After 5 days in culture, the slides were washed, the cells removed by washing with bleach, and the slides washed again with buffer. Cells that had been infected with full-length RANK resorbed the $CaPO_4$ matrix as determined by numerous clear pits (also called resorptive lacunae), which were visualized by phase-contrast microscopy. The number of pits in the $CaPO_4$ film is a measure of the extent to which the RANK-L induced the cells grown on that slide to differentiate into osteoclasts.

If desired, the $CaPO_4$ film can be stained using a 0.5% solution of alizarin red for 4 to 5 minutes followed by washing in water. After staining, the resorptive lacunae are visualized by phase contrast microscopy as a clear area on a red background.

Cells that have been differentiated using the full-length RANK transgene contained high levels of $CaPO_4$ resorption. While cells differentiated with either a control virus (encoding lacZ) or with the RANK construct lacking the TRAF6 binding domain (RANK D340–421) had insignificant levels of $CaPO_4$ resorption.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for screening for a molecule that agonizes or antagonizes RANK activity in cells expressing RANK, wherein RANK is a polypeptide that is capable of activating NF-κB and that is selected from the group consisting of: i) amino acids 1–616 of SEQ ID NO:2; ii) amino acids 1–625 of SEQ ID NO:4; and iii) a polypeptide having an at least 90% amino acid sequence identity with (i) or (ii), said method comprising the steps of:
   (a) contacting a candidate molecule with cells expressing RANK, said RANK expressing cells comprising a nucleic acid molecule encoding a reporter protein, said nucleic acid molecule being operably linked to a RANK-responsive regulatory nucleic acid sequence that is selected from the group consisting of a human or murine MMP-9 promoter and a human or murine TRAP promoter, wherein the cells are exposed to a RANK trigger prior to, during or after being contacted with said candidate molecule;
   (b) determining whether the level of reporter molecule expression in the contacted cells is enhanced or reduced as compared with the level of reporter molecule expression in a culture of reference RANK expressing cells that are not contacted with the candidate molecule; and
   (c) identifying the candidate molecule as a RANK agonist if the level of reporter molecule expression in the contacted cells is comparatively enhanced and identifying the candidate molecule as an RANK antagonist if the level of reporter molecule expression in the contacted cells is comparatively reduced.

2. The method of claim 1, wherein RANK is triggered in the RANK expressing cells by a method selected from the group consisting of:
   (a) contacting the cells with a RANK-L polypeptide, wherein the RANK-L polypeptide comprises amino acids 162–317 of SEQ ID NO:6;
   (b) contacting the cells with an agonistic anti-RANK antibody;
   (c) contacting the cells with cells that express RANK-L, wherein RANK-L is a polypeptide that comprises amino acids 162–317 of SEQ ID NO:6; and
   (d) overexpressing RANK in said RANK expressing cells.

3. The method of claim 2, wherein RANK is triggered in the RANK expressing cells by contacting the cells with a RANK-L polypeptide comprising amino acids 162–317 of SEQ ID NO:6 , and further wherein said RANK-L polypeptide is selected from the group consisting of native RANK-L, a leucine zipper fusion of RANK-L, and a FLAG polyHis fusion of RANK-L.

4. The method of claim 1, wherein the RANK responsive regulatory nucleic acid is a MMP-9 promoter.

5. The method of claim 4, wherein the MMP-9 promoter comprises nucleotides 1769–3591 of SEQ ID NO:11.

6. The method of claim 1 wherein the step of contacting RANK expressing cells with a candidate molecule comprises expressing in said cells an introduced DNA molecule that encodes a candidate nucleic acid molecule or a candidate protein molecule.

7. The method of claim 6 wherein said introduced DNA molecule is a cDNA molecule.

8. The method of claim 6 wherein said introduced DNA molecule is integrated into the genome of said cells.

9. The method of claim 6 wherein said introduced DNA molecule is not integrated into the genome of said cells.

10. The method of claim 6 wherein said candidate molecule is a protein encoded by the introduced DNA molecule.

11. The method of claim 6 wherein said candidate molecule is a nucleic acid molecule encoded by the introduced DNA molecule.

12. The method of claim 11 wherein said nucleic acid molecule possesses ribozyme activity.

13. The method of claim 6, further comprising isolating said introduced DNA molecule from a colony formed from said contacted cells.

14. The method of claim 1, wherein the step of contacting RANK expressing cells with a candidate molecule comprises culturing said cells in the presence of the candidate molecule, and further wherein said candidate molecule is a protein.

15. The method of claim 1, wherein the step of contacting RANK expressing cells with a candidate molecule comprises culturing said cells in the presence of said candidate molecule.

16. The method of claim 1, wherein said reporter molecule is selected from the group consisting of luciferase, green fluorescent protein, alkaline phosphatase and a heterologous surface protein.

17. The method of claim 16, wherein the reporter molecule is a heterologous surface protein that is selected from the group consisting of human IL-2 receptor, murine IL-4 receptor, human CD2 protein, human CD4 protein, human CD8 protein, luciferase protein, β-galactosidase, and green fluorescent protein.

18. The method of claim 1, wherein said RANK expressing cells express a defective RANK molecule and wherein said screening is for an agonist that complements said defective RANK activity.

19. The method of claim 1, wherein said RANK expressing cells are hematopoietic cells.

20. The method of claim 1, wherein said RANK expressing cells are RAW 264.7 cells.

21. The method of claim 1, further comprising the step of purifying the candidate molecule from cells in which the level of expressed reporter molecule is determined to be comparatively enhanced or reduced.

22. The method of claim 1, wherein the level of reporter molecule expression is determined by an assay selected from the group consisting of a fluorescence-based assay, a solid phase assay, and an assay employing a radioactive compound.

23. The method of claim 1, wherein determining the level of expressed reporter molecule comprises physically isolating by fluorescence-based cell sorting the cells that are expressing said reporter molecule.

24. A method according to claim 1, wherein the MMP-9 promoter is a murine promoter comprising nucleotides 1769–3591 of SEQ ID NO:11 and the TRAP promoter is a murine promoter comprising nucleotides 1–1991 of SEQ ID NO:12.

25. A method for screening for a molecule that agonizes or antagonizes RANK activity, said method comprising the steps of:
   (a) contacting a candidate molecule with cells expressing a defective RANK polypeptide consisting of amino acids 1–622 of SEQ ID NO:10, said cells comprising a nucleic acid molecule encoding a reporter protein, said nucleic acid molecule being operably linked to a RANK-responsive regulatory nucleic acid sequence that is selected from the group consisting of a human or murine MMP-9 promoter and a human or murine TRAP promoter;

(b) determining whether the level of reporter molecule expression in the contacted cells is enhanced or reduced as compared with the level of reporter molecule expression in a culture of reference cells expressing said defective RANK and comprising said nucleic acid molecule that are not contacted with the candidate molecule; and (c) identifying the candidate molecule as a RANK agonist if the level of reporter molecule expression in the contacted cells is comparatively enhanced and identifying the candidate molecule as a RANK antagonist if the level of reporter molecule expression in the contacted cells is comparatively reduced.

* * * * *

SEQUENCE LISTING

<160> NUMBER OF SEQ ID NOS: 13

<210> SEQ ID NO 1
<211> LENGTH: 3136
<212> TYPE: DNA
<213> ORGANISM: Homo sapiens
<220> FEATURE:
<221> NAME/KEY: CDS
<222> LOCATION: (39)..(1886)
<223> OTHER INFORMATION:

<400> SEQUENCE: 1

```
ccgctgaggc cgcggcgccc gccagcctgt cccgcgcc atg gcc ccg cgc gcc cgg         56
                                          Met Ala Pro Arg Ala Arg
                                          1               5 cgg cgc cgc ccg ctg ttc gcg ctg ctg ctc tgc gcg ctc ctc gcc              104
Arg Arg Arg Pro Leu Phe Ala Leu Leu Leu Cys Ala Leu Leu Ala
            10                  15                  20 cgg ctg cag gtg gct ttg cag atc gct cct cca tgt acc agt gag aag         152
Arg Leu Gln Val Ala Leu Gln Ile Ala Pro Pro Cys Thr Ser Glu Lys
        25                  30                  35 cat tat gag cat ctg gga cgg tgc tgt aac aaa tgt gaa cca gga aag         200
His Tyr Glu His Leu Gly Arg Cys Cys Asn Lys Cys Glu Pro Gly Lys
    40                  45                  50 tac atg tct tct aaa tgc act act acc tct gac agt gta tgt ctg ccc         248
Tyr Met Ser Ser Lys Cys Thr Thr Thr Ser Asp Ser Val Cys Leu Pro
55                  60                  65                  70 tgt ggc ccg gat gaa tac ttg gat agc tgg aat gaa gaa gat aaa tgc         296
Cys Gly Pro Asp Glu Tyr Leu Asp Ser Trp Asn Glu Glu Asp Lys Cys
                75                  80                  85 ttg ctg cat aaa gtt tgt gat aca ggc aag gcc ctg gtg gcc gtg gtc         344
Leu Leu His Lys Val Cys Asp Thr Gly Lys Ala Leu Val Ala Val Val
            90                  95                  100 gcc ggc aac agc acg acc ccc cgg cgc tgc gcg tgc acg gct ggg tac         392
Ala Gly Asn Ser Thr Thr Pro Arg Arg Cys Ala Cys Thr Ala Gly Tyr
        105                 110                 115 cac tgg agc cag gac tgc gag tgc tgc cgc cgc aac acc gag tgc gcg         440
His Trp Ser Gln Asp Cys Glu Cys Cys Arg Arg Asn Thr Glu Cys Ala
    120                 125                 130 ccg ggc ctg ggc gcc cag cac ccg ttg cag ctc aac aag gac aca gtg         488
Pro Gly Leu Gly Ala Gln His Pro Leu Gln Leu Asn Lys Asp Thr Val
135                 140                 145                 150
```

-continued

```
tgc aaa cct tgc ctt gca ggc tac ttc tct gat gcc ttt tcc tcc acg         536
Cys Lys Pro Cys Leu Ala Gly Tyr Phe Ser Asp Ala Phe Ser Ser Thr
            155                 160                 165 gac aaa tgc aga ccc tgg acc aac tgt acc ttc ctt gga aag aga gta         584
Asp Lys Cys Arg Pro Trp Thr Asn Cys Thr Phe Leu Gly Lys Arg Val
        170                 175                 180 gaa cat cat ggg aca gag aaa tcc gat gcg gtt tgc agt tct tct ctg         632
Glu His His Gly Thr Glu Lys Ser Asp Ala Val Cys Ser Ser Ser Leu
            185                 190                 195 cca gct aga aaa cca cca aat gaa ccc cat gtt tac ttg ccc ggt tta         680
Pro Ala Arg Lys Pro Pro Asn Glu Pro His Val Tyr Leu Pro Gly Leu
    200                 205                 210 ata att ctg ctt ctc ttc gcg tct gtg gcc ctg gtg gct gcc atc atc         728
Ile Ile Leu Leu Leu Phe Ala Ser Val Ala Leu Val Ala Ala Ile Ile
215                 220                 225                 230 ttt ggc gtt tgc tat agg aaa aaa ggg aaa gca ctc aca gct aat ttg         776
Phe Gly Val Cys Tyr Arg Lys Lys Gly Lys Ala Leu Thr Ala Asn Leu
                235                 240                 245 tgg cac tgg atc aat gag gct tgt ggc cgc cta agt gga gat aag gag         824
Trp His Trp Ile Asn Glu Ala Cys Gly Arg Leu Ser Gly Asp Lys Glu
            250                 255                 260 tcc tca ggt gac agt tgt gtc agt aca cac acg gca aac ttt ggt cag         872
Ser Ser Gly Asp Ser Cys Val Ser Thr His Thr Ala Asn Phe Gly Gln
        265                 270                 275 cag gga gca tgt gaa ggt gtc tta ctg ctg act ctg gag gag aag aca         920
Gln Gly Ala Cys Glu Gly Val Leu Leu Leu Thr Leu Glu Glu Lys Thr
    280                 285                 290 ttt cca gaa gat atg tgc tac cca gat caa ggt ggt gtc tgt cag ggc         968
Phe Pro Glu Asp Met Cys Tyr Pro Asp Gln Gly Gly Val Cys Gln Gly
295                 300                 305                 310 acg tgt gta gga ggt ggt ccc tac gca caa ggc gaa gat gcc agg atg        1016
Thr Cys Val Gly Gly Gly Pro Tyr Ala Gln Gly Glu Asp Ala Arg Met
                315                 320                 325 ctc tca ttg gtc agc aag acc gag ata gag gaa gac agc ttc aga cag        1064
Leu Ser Leu Val Ser Lys Thr Glu Ile Glu Glu Asp Ser Phe Arg Gln
            330                 335                 340 atg ccc aca gaa gat gaa tac atg gac agg ccc tcc cag ccc aca gac        1112
Met Pro Thr Glu Asp Glu Tyr Met Asp Arg Pro Ser Gln Pro Thr Asp
        345                 350                 355 cag tta ctg ttc ctc act gag cct gga agc aaa tcc aca cct cct ttc        1160
Gln Leu Leu Phe Leu Thr Glu Pro Gly Ser Lys Ser Thr Pro Pro Phe
    360                 365                 370 tct gaa ccc ctg gag gtg ggg gag aat gac agt tta agc cag tgc ttc        1208
Ser Glu Pro Leu Glu Val Gly Glu Asn Asp Ser Leu Ser Gln Cys Phe
375                 380                 385                 390 acg ggg aca cag agc aca gtg gtt tca gaa agc tgc aac tgc act gag        1256
Thr Gly Thr Gln Ser Thr Val Val Ser Glu Ser Cys Asn Cys Thr Glu
                395                 400                 405 ccc ctg tgc agg act gat tgg act ccc atg tcc tct gaa aac tac ttg        1304
Pro Leu Cys Arg Thr Asp Trp Thr Pro Met Ser Ser Glu Asn Tyr Leu
            410                 415                 420 caa aaa gag gtg gac agt ggc cat tgc ccg cac tgg gca gcc agc ccc        1352
Gln Lys Glu Val Asp Ser Gly His Cys Pro His Trp Ala Ala Ser Pro
        425                 430                 435 agc ccc aac tgg gca gat gtc tgc aca ggc tgc cgg aac cct cct ggg        1400
Ser Pro Asn Trp Ala Asp Val Cys Thr Gly Cys Arg Asn Pro Pro Gly
    440                 445                 450 gag gac tgt gaa ccc ctc gtg ggt tcc cca aaa cgt gga ccc ttg ccc        1448
Glu Asp Cys Glu Pro Leu Val Gly Ser Pro Lys Arg Gly Pro Leu Pro
```

```
                                                                    -continued
455                 460                 465                 470
cag tgc gcc tat ggc atg ggc ctt ccc cct gaa gaa gaa gcc agc agg    1496
Gln Cys Ala Tyr Gly Met Gly Leu Pro Pro Glu Glu Glu Ala Ser Arg
                475                 480                 485 acg gag gcc aga gac cag ccc gag gat ggg gct gat ggg agg ctc cca    1544
Thr Glu Ala Arg Asp Gln Pro Glu Asp Gly Ala Asp Gly Arg Leu Pro
            490                 495                 500 agc tca gcg agg gca ggt gcc ggg tct gga agc tcc cct ggt ggc cag    1592
Ser Ser Ala Arg Ala Gly Ala Gly Ser Gly Ser Ser Pro Gly Gly Gln
            505                 510                 515 tcc cct gca tct gga aat gtg act gga aac agt aac tcc acg ttc atc    1640
Ser Pro Ala Ser Gly Asn Val Thr Gly Asn Ser Asn Ser Thr Phe Ile
        520                 525                 530 tcc agc ggg cag gtg atg aac ttc aag ggc gac atc atc gtg gtc tac    1688
Ser Ser Gly Gln Val Met Asn Phe Lys Gly Asp Ile Ile Val Val Tyr
535                 540                 545                 550 gtc agc cag acc tcg cag gag ggc gcg gcg gcg gct gcg gag ccc atg    1736
Val Ser Gln Thr Ser Gln Glu Gly Ala Ala Ala Ala Ala Glu Pro Met
            555                 560                 565 ggc cgc ccg gtg cag gag gag acc ctg gcg cgc cga gac tcc ttc gcg    1784
Gly Arg Pro Val Gln Glu Glu Thr Leu Ala Arg Arg Asp Ser Phe Ala
        570                 575                 580 ggg aac ggc ccg cgc ttc ccg gac ccg tgc ggc ggc ccc gag ggg ctg    1832
Gly Asn Gly Pro Arg Phe Pro Asp Pro Cys Gly Gly Pro Glu Gly Leu
        585                 590                 595 cgg gag ccg gag aag gcc tcg agg ccg gtg cag gag caa ggc ggg gcc    1880
Arg Glu Pro Glu Lys Ala Ser Arg Pro Val Gln Glu Gln Gly Gly Ala
600                 605                 610 aag gct tgagcgcccc ccatggctgg gagcccgaag ctcggagcca gggctcgcga    1936
Lys Ala
615 gggcagcacc gcagcctctg ccccagcccc ggccacccag ggatcgatcg gtacagtcga    1996 ggaagaccac ccggcattct ctgcccactt tgccttccag gaaatgggct tttcaggaag    2056 tgaattgatg aggactgtcc ccatgcccac ggatgctcag cagcccgccg cactggggca    2116 gatgtctccc ctgccactcc tcaaactcgc agcagtaatt tgtggcacta tgacagctat    2176 ttttatgact atcctgttct gtggggggggg ggtctatgtt ttccccccat atttgtattc    2236 cttttcataa cttttcttga tatctttcct ccctcttttt taatgtaaag gttttctcaa    2296 aaattctcct aaaggtgagg gtctctttct tttctctttt cctttttttt ttcttttttt    2356 ggcaacctgg ctctggccca ggctagagtg cagtggtgcg attatagccc ggtgcagcct    2416 ctaactcctg ggctcaagca atccaagtga tcctcccacc tcaaccttcg gagtagctgg    2476 gatcacagct gcaggccacg cccagcttcc tcccccgac tcccccccc cagagacacg    2536 gtcccaccat gttacccagc ctggtctcaa actccccagc taaagcagtc ctccagcctc    2596 ggcctcccaa agtactggga ttacaggcgt gagcccccac gctggcctgc tttacgtatt    2656 ggcttttgtg ccctgctca cagtgtttta gagatggctt tcccagtgtg tgttcattgt    2716 aaacactttt gggaagggc taaacatgtg aggcctggag atagttgcta agttgctagg    2776 aacatgtggt gggactttca tattctgaaa aatgttctat attctcattt ttctaaaaga    2836 aagaaaaaag gaaacccgat ttatttctcc tgaatctttt taagtttgtg tcgttccta    2896 agcagaacta agctcagtat gtgaccttac ccgctaggtg gttaatttat ccatgctggc    2956 agaggcactc aggtacttgg taagcaaatt tctaaaactc caagttgctg cagcttggca    3016 ttcttcttat tctagaggtc tctctggaaa agatggagaa aatgaacagg acatgggggct    3076
```
cctggaaaga aagggcccgg gaagttcaag gaagaataaa gttgaaattt taaaaaaaaa    3136

<210> SEQ ID NO 2
<211> LENGTH: 616
<212> TYPE: PRT
<213> ORGANISM: Homo sapiens

<400> SEQUENCE: 2

Met Ala Pro Arg Ala Arg Arg Arg Pro Leu Phe Ala Leu Leu Leu
1               5                   10                  15

Leu Cys Ala Leu Leu Ala Arg Leu Gln Val Ala Leu Gln Ile Ala Pro
            20                  25                  30

Pro Cys Thr Ser Glu Lys His Tyr Glu His Leu Gly Arg Cys Cys Asn
        35                  40                  45

Lys Cys Glu Pro Gly Lys Tyr Met Ser Ser Lys Cys Thr Thr Thr Ser
    50                  55                  60

Asp Ser Val Cys Leu Pro Cys Gly Pro Asp Glu Tyr Leu Asp Ser Trp
65                  70                  75                  80

Asn Glu Glu Asp Lys Cys Leu Leu His Lys Val Cys Asp Thr Gly Lys
                85                  90                  95

Ala Leu Val Ala Val Ala Gly Asn Ser Thr Thr Pro Arg Arg Cys
            100                 105                 110

Ala Cys Thr Ala Gly Tyr His Trp Ser Gln Asp Cys Glu Cys Cys Arg
        115                 120                 125

Arg Asn Thr Glu Cys Ala Pro Gly Leu Gly Ala Gln His Pro Leu Gln
    130                 135                 140

Leu Asn Lys Asp Thr Val Cys Lys Pro Cys Leu Ala Gly Tyr Phe Ser
145                 150                 155                 160

Asp Ala Phe Ser Ser Thr Asp Lys Cys Arg Pro Trp Thr Asn Cys Thr
                165                 170                 175

Phe Leu Gly Lys Arg Val Glu His His Gly Thr Glu Lys Ser Asp Ala
            180                 185                 190

Val Cys Ser Ser Ser Leu Pro Ala Arg Lys Pro Pro Asn Glu Pro His
        195                 200                 205

Val Tyr Leu Pro Gly Leu Ile Ile Leu Leu Leu Phe Ala Ser Val Ala
    210                 215                 220

Leu Val Ala Ala Ile Ile Phe Gly Val Cys Tyr Arg Lys Lys Gly Lys
225                 230                 235                 240

Ala Leu Thr Ala Asn Leu Trp His Trp Ile Asn Glu Ala Cys Gly Arg
                245                 250                 255

Leu Ser Gly Asp Lys Glu Ser Ser Gly Asp Ser Cys Val Ser Thr His
            260                 265                 270

Thr Ala Asn Phe Gly Gln Gln Gly Ala Cys Glu Gly Val Leu Leu Leu
        275                 280                 285

Thr Leu Glu Glu Lys Thr Phe Pro Glu Asp Met Cys Tyr Pro Asp Gln
    290                 295                 300

Gly Gly Val Cys Gln Gly Thr Cys Val Gly Gly Pro Tyr Ala Gln
305                 310                 315                 320

Gly Glu Asp Ala Arg Met Leu Ser Leu Val Ser Lys Thr Glu Ile Glu
                325                 330                 335

Glu Asp Ser Phe Arg Gln Met Pro Thr Glu Asp Glu Tyr Met Asp Arg
            340                 345                 350

Pro Ser Gln Pro Thr Asp Gln Leu Leu Phe Leu Thr Glu Pro Gly Ser

-continued

```
                       355                 360                 365
Lys Ser Thr Pro Pro Phe Ser Glu Pro Leu Glu Val Gly Glu Asn Asp
        370                 375                 380

Ser Leu Ser Gln Cys Phe Thr Gly Thr Gln Ser Thr Val Gly Ser Glu
385                 390                 395                 400

Ser Cys Asn Cys Thr Glu Pro Leu Cys Arg Thr Asp Trp Thr Pro Met
                405                 410                 415

Ser Ser Glu Asn Tyr Leu Gln Lys Glu Val Asp Ser Gly His Cys Pro
            420                 425                 430

His Trp Ala Ala Ser Pro Ser Pro Asn Trp Ala Asp Val Cys Thr Gly
        435                 440                 445

Cys Arg Asn Pro Pro Gly Glu Asp Cys Glu Pro Leu Val Gly Ser Pro
450                 455                 460

Lys Arg Gly Pro Leu Pro Gln Cys Ala Tyr Gly Met Gly Leu Pro Pro
465                 470                 475                 480

Glu Glu Glu Ala Ser Arg Thr Glu Ala Arg Asp Gln Pro Glu Asp Gly
                485                 490                 495

Ala Asp Gly Arg Leu Pro Ser Ser Ala Arg Ala Gly Ala Gly Ser Gly
            500                 505                 510

Ser Ser Pro Gly Gly Gln Ser Pro Ala Ser Gly Asn Val Thr Gly Asn
        515                 520                 525

Ser Asn Ser Thr Phe Ile Ser Ser Gly Gln Val Met Asn Phe Lys Gly
    530                 535                 540

Asp Ile Ile Val Val Tyr Val Ser Gln Thr Ser Gln Glu Gly Ala Ala
545                 550                 555                 560

Ala Ala Ala Glu Pro Met Gly Arg Pro Val Gln Glu Glu Thr Leu Ala
                565                 570                 575

Arg Arg Asp Ser Phe Ala Gly Asn Gly Pro Arg Phe Pro Asp Pro Cys
            580                 585                 590

Gly Gly Pro Glu Gly Leu Arg Glu Pro Glu Lys Ala Ser Arg Pro Val
        595                 600                 605

Gln Glu Gln Gly Gly Ala Lys Ala
    610                 615

<210> SEQ ID NO 3
<211> LENGTH: 1878
<212> TYPE: DNA
<213> ORGANISM: Mus sp.
<220> FEATURE:
<221> NAME/KEY: CDS
<222> LOCATION: (1)..(1875)
<223> OTHER INFORMATION:

<400> SEQUENCE: 3 atg gcc ccg cgc gcc cgg cgg cgc cgc cag ctg ccc gcg ccg ctg ctg      48
Met Ala Pro Arg Ala Arg Arg Arg Arg Gln Leu Pro Ala Pro Leu Leu
1               5                   10                  15 gcg ctc tgc gtg ctg ctc gtt cca ctg cag gtg act ctc cag gtc act      96
Ala Leu Cys Val Leu Leu Val Pro Leu Gln Val Thr Leu Gln Val Thr
            20                  25                  30 cct cca tgc acc cag gag agg cat tat gag cat ctc gga cgg tgt tgc     144
Pro Pro Cys Thr Gln Glu Arg His Tyr Glu His Leu Gly Arg Cys Cys
        35                  40                  45 agc aga tgc gaa cca gga aag tac ctg tcc tct aag tgc act cct acc     192
Ser Arg Cys Glu Pro Gly Lys Tyr Leu Ser Ser Lys Cys Thr Pro Thr
    50                  55                  60 tcc gac agt gtg tgt ctg ccc tgt ggc ccc gat gag tac ttg gac acc     240
```

-continued

| | | | | | | | | | | | | | | | | |
|---|---|---|---|---|---|---|---|---|---|---|---|---|---|---|---|---|
| Ser<br>65 | Asp | Ser | Val | Cys<br>70 | Leu | Pro | Cys | Gly | Pro<br>75 | Asp | Glu | Tyr | Leu | Asp<br>80 | Thr | |
| tgg<br>Trp | aat<br>Asn | gaa<br>Glu | gaa<br>Glu | gat<br>Asp<br>85 | aaa<br>Lys | tgc<br>Cys | ttg<br>Leu | ctg<br>Leu | cat<br>His<br>90 | aaa<br>Lys | gtc<br>Val | tgt<br>Cys | gat<br>Asp<br>95 | gca<br>Ala | ggc<br>Gly | 288 |
| aag<br>Lys | gcc<br>Ala | ctg<br>Leu<br>100 | gtg<br>Val | gcg<br>Ala | gtg<br>Val | gat<br>Asp | cct<br>Pro<br>105 | ggc<br>Gly | aac<br>Asn | cac<br>His | acg<br>Thr | gcc<br>Ala<br>110 | ccg<br>Pro | cgt<br>Arg | cgc<br>Arg | 336 |
| tgt<br>Cys | gct<br>Ala | tgc<br>Cys<br>115 | acg<br>Thr | gct<br>Ala | ggc<br>Gly | tac<br>Tyr | cac<br>His<br>120 | tgg<br>Trp | aac<br>Asn | tca<br>Ser | gac<br>Asp | tgc<br>Cys<br>125 | gag<br>Glu | tgc<br>Cys | tgc<br>Cys | 384 |
| cgc<br>Arg | agg<br>Arg<br>130 | aac<br>Asn | acg<br>Thr | gag<br>Glu | tgt<br>Cys | gca<br>Ala<br>135 | cct<br>Pro | ggc<br>Gly | ttc<br>Phe | gga<br>Gly | gct<br>Ala<br>140 | cag<br>Gln | cat<br>His | ccc<br>Pro | ttg<br>Leu | 432 |
| cag<br>Gln<br>145 | ctc<br>Leu | aac<br>Asn | aag<br>Lys | gat<br>Asp<br>150 | acg<br>Thr | gtg<br>Val | tgc<br>Cys | aca<br>Thr | ccc<br>Pro<br>155 | tgc<br>Cys | ctc<br>Leu | ctg<br>Leu | ggc<br>Gly | ttc<br>Phe<br>160 | ttc<br>Phe | 480 |
| tca<br>Ser | gat<br>Asp | gtc<br>Val | ttt<br>Phe | tcg<br>Ser<br>165 | tcc<br>Ser | aca<br>Thr | gac<br>Asp | aaa<br>Lys | tgc<br>Cys<br>170 | aaa<br>Lys | cct<br>Pro | tgg<br>Trp | acc<br>Thr | aac<br>Asn<br>175 | tgc<br>Cys | 528 |
| acc<br>Thr | ctc<br>Leu | ctt<br>Leu<br>180 | gga<br>Gly | aag<br>Lys | cta<br>Leu | gaa<br>Glu | gca<br>Ala<br>185 | cac<br>His | cag<br>Gln | ggg<br>Gly | aca<br>Thr | acg<br>Thr<br>190 | gaa<br>Glu | tca<br>Ser | gat<br>Asp | 576 |
| gtg<br>Val | gtc<br>Val | tgc<br>Cys<br>195 | agc<br>Ser | tct<br>Ser | tcc<br>Ser | atg<br>Met | aca<br>Thr<br>200 | ctg<br>Leu | agg<br>Arg | aga<br>Arg | cca<br>Pro | ccc<br>Pro<br>205 | aag<br>Lys | gag<br>Glu | gcc<br>Ala | 624 |
| cag<br>Gln | gct<br>Ala<br>210 | tac<br>Tyr | ctg<br>Leu | ccc<br>Pro | agt<br>Ser | ctc<br>Leu<br>215 | atc<br>Ile | gtt<br>Val | ctg<br>Leu | ctc<br>Leu | ctc<br>Leu<br>220 | ttc<br>Phe | atc<br>Ile | tct<br>Ser | gtg<br>Val | 672 |
| gta<br>Val<br>225 | gta<br>Val | gtg<br>Val | gct<br>Ala | gcc<br>Ala<br>230 | atc<br>Ile | atc<br>Ile | ttc<br>Phe | ggc<br>Gly | gtt<br>Val<br>235 | tac<br>Tyr | tac<br>Tyr | agg<br>Arg | aag<br>Lys | gga<br>Gly<br>240 | ggg<br>Gly | 720 |
| aaa<br>Lys | gcg<br>Ala | ctg<br>Leu | aca<br>Thr | gct<br>Ala<br>245 | aat<br>Asn | ttg<br>Leu | tgg<br>Trp | aat<br>Asn | tgg<br>Trp<br>250 | gtc<br>Val | aat<br>Asn | gat<br>Asp | gct<br>Ala | tgc<br>Cys<br>255 | agt<br>Ser | 768 |
| agt<br>Ser | cta<br>Leu | agt<br>Ser<br>260 | gga<br>Gly | aat<br>Asn | aag<br>Lys | gag<br>Glu | tcc<br>Ser<br>265 | tca<br>Ser | ggg<br>Gly | gac<br>Asp | cgt<br>Arg | tgt<br>Cys<br>270 | gct<br>Ala | ggt<br>Gly | tcc<br>Ser | 816 |
| cac<br>His | tcg<br>Ser<br>275 | gca<br>Ala | acc<br>Thr | tcc<br>Ser | agt<br>Ser | cag<br>Gln<br>280 | caa<br>Gln | gaa<br>Glu | gtg<br>Val | tgt<br>Cys | gaa<br>Glu<br>285 | ggt<br>Gly | atc<br>Ile | tta<br>Leu | cta<br>Leu | 864 |
| atg<br>Met | act<br>Thr<br>290 | cgg<br>Arg | gag<br>Glu | gag<br>Glu | aag<br>Lys | atg<br>Met<br>295 | gtt<br>Val | cca<br>Pro | gaa<br>Glu | gac<br>Asp | ggt<br>Gly<br>300 | gct<br>Ala | gga<br>Gly | gtc<br>Val | tgt<br>Cys | 912 |
| ggg<br>Gly<br>305 | cct<br>Pro | gtg<br>Val | tgt<br>Cys | gcg<br>Ala<br>310 | gca<br>Ala | ggt<br>Gly | ggg<br>Gly | ccc<br>Pro | tgg<br>Trp<br>315 | gca<br>Ala | gaa<br>Glu | gtc<br>Val | aga<br>Arg | gat<br>Asp<br>320 | tct<br>Ser | 960 |
| agg<br>Arg | acg<br>Thr | ttc<br>Phe | aca<br>Thr | ctg<br>Leu<br>325 | gtc<br>Val | agc<br>Ser | gag<br>Glu | gtt<br>Val | gag<br>Glu<br>330 | acg<br>Thr | caa<br>Gln | gga<br>Gly | gac<br>Asp | ctc<br>Leu<br>335 | tcg<br>Ser | 1008 |
| agg<br>Arg | aag<br>Lys | att<br>Ile | ccc<br>Pro | aca<br>Thr<br>340 | gag<br>Glu | gat<br>Asp | gag<br>Glu | tac<br>Tyr | acg<br>Thr<br>345 | gac<br>Asp | cgg<br>Arg | ccc<br>Pro | tcg<br>Ser<br>350 | cag<br>Gln | cct<br>Pro | 1056 |
| tcg<br>Ser | act<br>Thr | ggt<br>Gly<br>355 | tca<br>Ser | ctg<br>Leu | ctc<br>Leu | cta<br>Leu | atc<br>Ile<br>360 | cag<br>Gln | cag<br>Gln | gga<br>Gly | agc<br>Ser | aaa<br>Lys<br>365 | tct<br>Ser | ata<br>Ile | ccc<br>Pro | 1104 |
| cca<br>Pro | ttc<br>Phe<br>370 | cag<br>Gln | gag<br>Glu | ccc<br>Pro | ctg<br>Leu | gaa<br>Glu<br>375 | gtg<br>Val | ggg<br>Gly | gag<br>Glu | aac<br>Asn | gac<br>Asp<br>380 | agt<br>Ser | tta<br>Leu | agc<br>Ser | cag<br>Gln | 1152 |

```
tgt ttc acc ggg act gaa agc acg gtg gat tct gag ggc tgt gac ttc      1200
Cys Phe Thr Gly Thr Glu Ser Thr Val Asp Ser Glu Gly Cys Asp Phe
385                 390                 395                 400 act gag cct ccg agc aga act gac tct atg ccc gtg tcc cct gaa aag      1248
Thr Glu Pro Pro Ser Arg Thr Asp Ser Met Pro Val Ser Pro Glu Lys
                405                 410                 415 cac ctg aca aaa gaa ata gaa ggt gac agt tgc ctc ccc tgg gtg gtc      1296
His Leu Thr Lys Glu Ile Glu Gly Asp Ser Cys Leu Pro Trp Val Val
420                 425                 430 agc tcc aac tca aca gat ggc tac aca ggc agt ggg aac act cct ggg      1344
Ser Ser Asn Ser Thr Asp Gly Tyr Thr Gly Ser Gly Asn Thr Pro Gly
            435                 440                 445 gag gac cat gaa ccc ttt cca ggg tcc ctg aaa tgt gga cca ttg ccc      1392
Glu Asp His Glu Pro Phe Pro Gly Ser Leu Lys Cys Gly Pro Leu Pro
450                 455                 460 cag tgt gcc tac agc atg ggc ttt ccc agt gaa gca gca gcc agc atg      1440
Gln Cys Ala Tyr Ser Met Gly Phe Pro Ser Glu Ala Ala Ala Ser Met
465                 470                 475                 480 gca gag gcg gga gta cgg ccc cag gac agg gct gat gag agg gga gcc      1488
Ala Glu Ala Gly Val Arg Pro Gln Asp Arg Ala Asp Glu Arg Gly Ala
                485                 490                 495 tca ggg tcc ggg agc tcc ccc agt gac cag cca cct gcc tct ggg aac      1536
Ser Gly Ser Gly Ser Ser Pro Ser Asp Gln Pro Pro Ala Ser Gly Asn
            500                 505                 510 gtg act gga aac agt aac tcc acg ttc atc tct agc ggg cag gtg atg      1584
Val Thr Gly Asn Ser Asn Ser Thr Phe Ile Ser Ser Gly Gln Val Met
        515                 520                 525 aac ttc aag ggt gac atc atc gtg gtg tat gtc agc cag acc tcg cag      1632
Asn Phe Lys Gly Asp Ile Ile Val Val Tyr Val Ser Gln Thr Ser Gln
530                 535                 540 gag ggc ccg ggt tcc gca gag ccc gag tcg gag ccc gtg ggc cgc cct      1680
Glu Gly Pro Gly Ser Ala Glu Pro Glu Ser Glu Pro Val Gly Arg Pro
545                 550                 555                 560 gtg cag gag gag acg ctg gca cac aga gac tcc ttt gcg ggc acc gcg      1728
Val Gln Glu Glu Thr Leu Ala His Arg Asp Ser Phe Ala Gly Thr Ala
                565                 570                 575 ccg cgc ttc ccc gac gtc tgt gcc acc ggg gct ggg ctg cag gag cag      1776
Pro Arg Phe Pro Asp Val Cys Ala Thr Gly Ala Gly Leu Gln Glu Gln
            580                 585                 590 ggg gca ccc cgg cag aag gac ggg aca tcg cgg ccg gtg cag gag cag      1824
Gly Ala Pro Arg Gln Lys Asp Gly Thr Ser Arg Pro Val Gln Glu Gln
        595                 600                 605 ggt ggg gcg cag act tca ctc cat acc cag ggg tcc gga caa tgt gca      1872
Gly Gly Ala Gln Thr Ser Leu His Thr Gln Gly Ser Gly Gln Cys Ala
610                 615                 620 gaa tga                                                              1878
Glu
625

<210> SEQ ID NO 4
<211> LENGTH: 625
<212> TYPE: PRT
<213> ORGANISM: Mus sp.

<400> SEQUENCE: 4

Met Ala Pro Arg Ala Arg Arg Arg Gln Leu Pro Ala Pro Leu Leu
1               5                   10                  15

Ala Leu Cys Val Leu Leu Val Pro Leu Gln Val Thr Leu Gln Val Thr
                20                  25                  30

Pro Pro Cys Thr Gln Glu Arg His Tyr Glu His Leu Gly Arg Cys Cys
```

-continued

```
                35                  40                  45
Ser Arg Cys Glu Pro Gly Lys Tyr Leu Ser Ser Lys Cys Thr Pro Thr
 50                  55                  60

Ser Asp Ser Val Cys Leu Pro Cys Gly Pro Asp Glu Tyr Leu Asp Thr
65                   70                  75                  80

Trp Asn Glu Glu Asp Lys Cys Leu Leu His Lys Val Cys Asp Ala Gly
                 85                  90                  95

Lys Ala Leu Val Ala Val Asp Pro Gly Asn His Thr Ala Pro Arg Arg
                100                 105                 110

Cys Ala Cys Thr Ala Gly Tyr His Trp Asn Ser Asp Cys Glu Cys Cys
                115                 120                 125

Arg Arg Asn Thr Glu Cys Ala Pro Gly Phe Gly Ala Gln His Pro Leu
130                 135                 140

Gln Leu Asn Lys Asp Thr Val Cys Thr Pro Cys Leu Leu Gly Phe Phe
145                 150                 155                 160

Ser Asp Val Phe Ser Ser Thr Asp Lys Cys Lys Pro Trp Thr Asn Cys
                165                 170                 175

Thr Leu Leu Gly Lys Leu Glu Ala His Gln Gly Thr Thr Glu Ser Asp
                180                 185                 190

Val Val Cys Ser Ser Ser Met Thr Leu Arg Arg Pro Pro Lys Glu Ala
                195                 200                 205

Gln Ala Tyr Leu Pro Ser Leu Ile Val Leu Leu Phe Ile Ser Val
                210                 215                 220

Val Val Val Ala Ala Ile Ile Phe Gly Val Tyr Tyr Arg Lys Gly Gly
225                 230                 235                 240

Lys Ala Leu Thr Ala Asn Leu Trp Asn Trp Val Asn Asp Ala Cys Ser
                245                 250                 255

Ser Leu Ser Gly Asn Lys Glu Ser Ser Gly Asp Arg Cys Ala Gly Ser
                260                 265                 270

His Ser Ala Thr Ser Ser Gln Gln Glu Val Cys Glu Gly Ile Leu Leu
                275                 280                 285

Met Thr Arg Glu Glu Lys Met Val Pro Glu Asp Gly Ala Gly Val Cys
290                 295                 300

Gly Pro Val Cys Ala Ala Gly Gly Pro Trp Ala Glu Val Arg Asp Ser
305                 310                 315                 320

Arg Thr Phe Thr Leu Val Ser Glu Val Glu Thr Gln Gly Asp Leu Ser
                325                 330                 335

Arg Lys Ile Pro Thr Glu Asp Glu Tyr Thr Asp Arg Pro Ser Gln Pro
                340                 345                 350

Ser Thr Gly Ser Leu Leu Leu Ile Gln Gln Gly Ser Lys Ser Ile Pro
                355                 360                 365

Pro Phe Gln Glu Pro Leu Glu Val Gly Glu Asn Asp Ser Leu Ser Gln
                370                 375                 380

Cys Phe Thr Gly Thr Glu Ser Thr Val Asp Ser Glu Gly Cys Asp Phe
385                 390                 395                 400

Thr Glu Pro Pro Ser Arg Thr Asp Ser Met Pro Val Ser Pro Glu Lys
                405                 410                 415

His Leu Thr Lys Glu Ile Glu Gly Asp Ser Cys Leu Pro Trp Val Val
                420                 425                 430

Ser Ser Asn Ser Thr Asp Gly Tyr Thr Gly Ser Gly Asn Thr Pro Gly
                435                 440                 445

Glu Asp His Glu Pro Phe Pro Gly Ser Leu Lys Cys Gly Pro Leu Pro
450                 455                 460
```

```
Gln Cys Ala Tyr Ser Met Gly Phe Pro Ser Glu Ala Ala Ser Met
465                 470                 475                 480

Ala Glu Ala Gly Val Arg Pro Gln Asp Arg Ala Asp Glu Arg Gly Ala
                485                 490                 495

Ser Gly Ser Gly Ser Ser Pro Ser Asp Gln Pro Pro Ala Ser Gly Asn
            500                 505                 510

Val Thr Gly Asn Ser Asn Ser Thr Phe Ile Ser Gly Gln Val Met
        515                 520                 525

Asn Phe Lys Gly Asp Ile Ile Val Val Tyr Val Ser Gln Thr Ser Gln
    530                 535                 540

Glu Gly Pro Gly Ser Ala Glu Pro Glu Ser Glu Pro Val Gly Arg Pro
545                 550                 555                 560

Val Gln Glu Glu Thr Leu Ala His Arg Asp Ser Phe Ala Gly Thr Ala
                565                 570                 575

Pro Arg Phe Pro Asp Val Cys Ala Thr Gly Ala Gly Leu Gln Glu Gln
                580                 585                 590

Gly Ala Pro Arg Gln Lys Asp Gly Thr Ser Arg Pro Val Gln Glu Gln
            595                 600                 605

Gly Gly Ala Gln Thr Ser Leu His Thr Gln Gly Ser Gly Gln Cys Ala
    610                 615                 620

Glu
625

<210> SEQ ID NO 5
<211> LENGTH: 954
<212> TYPE: DNA
<213> ORGANISM: Homo sapiens
<220> FEATURE:
<221> NAME/KEY: CDS
<222> LOCATION: (1)..(951)
<223> OTHER INFORMATION:

<400> SEQUENCE: 5 atg cgc cgc gcc agc aga gac tac acc aag tac ctg cgt ggc tcg gag     48
Met Arg Arg Ala Ser Arg Asp Tyr Thr Lys Tyr Leu Arg Gly Ser Glu
1               5                   10                  15 gag atg ggc ggc ggc ccc gga gcc ccg cac gag ggc ccc ctg cac gcc     96
Glu Met Gly Gly Gly Pro Gly Ala Pro His Glu Gly Pro Leu His Ala
                20                  25                  30 ccg ccg ccg cct gcg ccg cac cag ccc ccc gcc gcc tcc cgc tcc atg    144
Pro Pro Pro Pro Ala Pro His Gln Pro Pro Ala Ala Ser Arg Ser Met
            35                  40                  45 ttc gtg gcc ctc ctg ggg ctg ggg ctg ggc cag gtt gtc tgc agc gtc    192
Phe Val Ala Leu Leu Gly Leu Gly Leu Gly Gln Val Val Cys Ser Val
    50                  55                  60 gcc ctg ttc ttc tat ttc aga gcg cag atg gat cct aat aga ata tca    240
Ala Leu Phe Phe Tyr Phe Arg Ala Gln Met Asp Pro Asn Arg Ile Ser
65                  70                  75                  80 gaa gat ggc act cac tgc att tat aga att ttg aga ctc cat gaa aat    288
Glu Asp Gly Thr His Cys Ile Tyr Arg Ile Leu Arg Leu His Glu Asn
                85                  90                  95 gca gat ttt caa gac aca act ctg gag agt caa gat aca aaa tta ata    336
Ala Asp Phe Gln Asp Thr Thr Leu Glu Ser Gln Asp Thr Lys Leu Ile
                100                 105                 110 cct gat tca tgt agg aga att aaa cag gcc ttt caa gga gct gtg caa    384
Pro Asp Ser Cys Arg Arg Ile Lys Gln Ala Phe Gln Gly Ala Val Gln
            115                 120                 125 aag gaa tta caa cat atc gtt gga tca cag cac atc aga gca gag aaa    432
```

```
Lys Glu Leu Gln His Ile Val Gly Ser Gln His Ile Arg Ala Glu Lys
            130                 135                 140 gcg atg gtg gat ggc tca tgg tta gat ctg gcc aag agg agc aag ctt       480
Ala Met Val Asp Gly Ser Trp Leu Asp Leu Ala Lys Arg Ser Lys Leu
145                 150                 155                 160 gaa gct cag cct ttt gct cat ctc act att aat gcc acc gac atc cca       528
Glu Ala Gln Pro Phe Ala His Leu Thr Ile Asn Ala Thr Asp Ile Pro
                165                 170                 175 tct ggt tcc cat aaa gtg agt ctg tcc tct tgg tac cat gat cgg ggt       576
Ser Gly Ser His Lys Val Ser Leu Ser Ser Trp Tyr His Asp Arg Gly
            180                 185                 190 tgg gcc aag atc tcc aac atg act ttt agc aat gga aaa cta ata gtt       624
Trp Ala Lys Ile Ser Asn Met Thr Phe Ser Asn Gly Lys Leu Ile Val
        195                 200                 205 aat cag gat ggc ttt tat tac ctg tat gcc aac att tgc ttt cga cat       672
Asn Gln Asp Gly Phe Tyr Tyr Leu Tyr Ala Asn Ile Cys Phe Arg His
    210                 215                 220 cat gaa act tca gga gac cta gct aca gag tat ctt caa cta atg gtg       720
His Glu Thr Ser Gly Asp Leu Ala Thr Glu Tyr Leu Gln Leu Met Val
225                 230                 235                 240 tac gtc act aaa acc agc atc aaa atc cca agt tct cat acc ctg atg       768
Tyr Val Thr Lys Thr Ser Ile Lys Ile Pro Ser Ser His Thr Leu Met
                245                 250                 255 aaa gga gga agc acc aag tat tgg tca ggg aat tct gaa ttc cat ttt       816
Lys Gly Gly Ser Thr Lys Tyr Trp Ser Gly Asn Ser Glu Phe His Phe
            260                 265                 270 tat tcc ata aac gtt ggt gga ttt ttt aag tta cgg tct gga gag gaa       864
Tyr Ser Ile Asn Val Gly Gly Phe Phe Lys Leu Arg Ser Gly Glu Glu
        275                 280                 285 atc agc atc gag gtc tcc aac ccc tcc tta ctg gat ccg gat cag gat       912
Ile Ser Ile Glu Val Ser Asn Pro Ser Leu Leu Asp Pro Asp Gln Asp
    290                 295                 300 gca aca tac ttt ggg gct ttt aaa gtt cga gat ata gat tga               954
Ala Thr Tyr Phe Gly Ala Phe Lys Val Arg Asp Ile Asp
305                 310                 315

<210> SEQ ID NO 6
<211> LENGTH: 317
<212> TYPE: PRT
<213> ORGANISM: Homo sapiens

<400> SEQUENCE: 6

Met Arg Arg Ala Ser Arg Asp Tyr Thr Lys Tyr Leu Arg Gly Ser Glu
1               5                   10                  15

Glu Met Gly Gly Gly Pro Gly Ala Pro His Glu Gly Pro Leu His Ala
            20                  25                  30

Pro Pro Pro Ala Pro His Gln Pro Pro Ala Ala Ser Arg Ser Met
        35                  40                  45

Phe Val Ala Leu Leu Gly Leu Gly Leu Gly Gln Val Val Cys Ser Val
    50                  55                  60

Ala Leu Phe Phe Tyr Phe Arg Ala Gln Met Asp Pro Asn Arg Ile Ser
65                  70                  75                  80

Glu Asp Gly Thr His Cys Ile Tyr Arg Ile Leu Arg Leu His Glu Asn
                85                  90                  95

Ala Asp Phe Gln Asp Thr Thr Leu Glu Ser Gln Asp Thr Lys Leu Ile
            100                 105                 110

Pro Asp Ser Cys Arg Arg Ile Lys Gln Ala Phe Gln Gly Ala Val Gln
        115                 120                 125
```

```
Lys Glu Leu Gln His Ile Val Gly Ser Gln His Ile Arg Ala Glu Lys
        130                 135                 140
Ala Met Val Asp Gly Ser Trp Leu Asp Leu Ala Lys Arg Ser Lys Leu
145                 150                 155                 160
Glu Ala Gln Pro Phe Ala His Leu Thr Ile Asn Ala Thr Asp Ile Pro
                165                 170                 175
Ser Gly Ser His Lys Val Ser Leu Ser Ser Trp Tyr His Asp Arg Gly
            180                 185                 190
Trp Ala Lys Ile Ser Asn Met Thr Phe Ser Asn Gly Lys Leu Ile Val
        195                 200                 205
Asn Gln Asp Gly Phe Tyr Tyr Leu Tyr Ala Asn Ile Cys Phe Arg His
210                 215                 220
His Glu Thr Ser Gly Asp Leu Ala Thr Glu Tyr Leu Gln Leu Met Val
225                 230                 235                 240
Tyr Val Thr Lys Thr Ser Ile Lys Ile Pro Ser Ser His Thr Leu Met
                245                 250                 255
Lys Gly Gly Ser Thr Lys Tyr Trp Ser Gly Asn Ser Glu Phe His Phe
            260                 265                 270
Tyr Ser Ile Asn Val Gly Gly Phe Phe Lys Leu Arg Ser Gly Glu Glu
        275                 280                 285
Ile Ser Ile Glu Val Ser Asn Pro Ser Leu Leu Asp Pro Asp Gln Asp
290                 295                 300
Ala Thr Tyr Phe Gly Ala Phe Lys Val Arg Asp Ile Asp
305                 310                 315
```

<210> SEQ ID NO 7
<211> LENGTH: 1694
<212> TYPE: DNA
<213> ORGANISM: Mus musculus
<220> FEATURE:
<221> NAME/KEY: CDS
<222> LOCATION: (1)..(948)
<223> OTHER INFORMATION:

<400> SEQUENCE: 7

```
atg cgc cgg gcc agc cga gac tac ggc aag tac ctg cgc agc tcg gag      48
Met Arg Arg Ala Ser Arg Asp Tyr Gly Lys Tyr Leu Arg Ser Ser Glu
1               5                   10                  15 gag atg ggc agc ggc ccc ggc gtc cca cac gag ggt ccg ctg cac ccc      96
Glu Met Gly Ser Gly Pro Gly Val Pro His Glu Gly Pro Leu His Pro
            20                  25                  30 gcg cct tct gca ccg gct ccg gcg ccg cca ccc gcc gcc tcc cgc tcc     144
Ala Pro Ser Ala Pro Ala Pro Ala Pro Pro Pro Ala Ala Ser Arg Ser
        35                  40                  45 atg ttc ctg gcc ctc ctg ggg ctg gga ctg ggc cag gtg gtc tgc agc     192
Met Phe Leu Ala Leu Leu Gly Leu Gly Leu Gly Gln Val Val Cys Ser
    50                  55                  60 atc gct ctg ttc ctg tac ttt cga gcg cag atg gat cct aac aga ata     240
Ile Ala Leu Phe Leu Tyr Phe Arg Ala Gln Met Asp Pro Asn Arg Ile
65                  70                  75                  80 tca gaa gac agc act cac tgc ttt tat aga atc ctg aga ctc cat gaa     288
Ser Glu Asp Ser Thr His Cys Phe Tyr Arg Ile Leu Arg Leu His Glu
                85                  90                  95 aac gca gat ttg cag gac tcg act ctg gag agt gaa gac aca cta cct     336
Asn Ala Asp Leu Gln Asp Ser Thr Leu Glu Ser Glu Asp Thr Leu Pro
            100                 105                 110 gac tcc tgc agg agg atg aaa caa gcc ttt cag ggg gcc gtg cag aag     384
Asp Ser Cys Arg Arg Met Lys Gln Ala Phe Gln Gly Ala Val Gln Lys
        115                 120                 125
```

```
gaa ctg caa cac att gtg ggg cca cag cgc ttc tca gga gct cca gct      432
Glu Leu Gln His Ile Val Gly Pro Gln Arg Phe Ser Gly Ala Pro Ala
    130                 135                 140 atg atg gaa ggc tca tgg ttg gat gtg gcc cag cga ggc aag cct gag      480
Met Met Glu Gly Ser Trp Leu Asp Val Ala Gln Arg Gly Lys Pro Glu
145                 150                 155                 160 gcc cag cca ttt gca cac ctc acc atc aat gct gcc agc atc cca tcg      528
Ala Gln Pro Phe Ala His Leu Thr Ile Asn Ala Ala Ser Ile Pro Ser
                165                 170                 175 ggt tcc cat aaa gtc act ctg tcc tct tgg tac cac gat cga ggc tgg      576
Gly Ser His Lys Val Thr Leu Ser Ser Trp Tyr His Asp Arg Gly Trp
            180                 185                 190 gcc aag atc tct aac atg acg tta agc aac gga aaa cta agg gtt aac      624
Ala Lys Ile Ser Asn Met Thr Leu Ser Asn Gly Lys Leu Arg Val Asn
        195                 200                 205 caa gat ggc ttc tat tac ctg tac gcc aac att tgc ttt cgg cat cat      672
Gln Asp Gly Phe Tyr Tyr Leu Tyr Ala Asn Ile Cys Phe Arg His His
    210                 215                 220 gaa aca tcg gga agc gta cct aca gac tat ctt cag ctg atg gtg tat      720
Glu Thr Ser Gly Ser Val Pro Thr Asp Tyr Leu Gln Leu Met Val Tyr
225                 230                 235                 240 gtc gtt aaa acc agc atc aaa atc cca agt tct cat aac ctg atg aaa      768
Val Val Lys Thr Ser Ile Lys Ile Pro Ser Ser His Asn Leu Met Lys
                245                 250                 255 gga ggg agc acg aaa aac tgg tcg ggc aat tct gaa ttc cac ttt tat      816
Gly Gly Ser Thr Lys Asn Trp Ser Gly Asn Ser Glu Phe His Phe Tyr
                260                 265                 270 tcc ata aat gtt ggg gga ttt ttc aag ctc cga gct ggt gaa gaa att      864
Ser Ile Asn Val Gly Gly Phe Phe Lys Leu Arg Ala Gly Glu Glu Ile
            275                 280                 285 agc att cag gtg tcc aac cct tcc ctg ctg gat ccg gat caa gat gcg      912
Ser Ile Gln Val Ser Asn Pro Ser Leu Leu Asp Pro Asp Gln Asp Ala
        290                 295                 300 acg tac ttt ggg gct ttc aaa gtt cag gac ata gac tgagactcat           958
Thr Tyr Phe Gly Ala Phe Lys Val Gln Asp Ile Asp
305                 310                 315 ttcgtggaac attagcatgg atgtcctaga tgtttggaaa cttcttaaaa aatggatgat   1018
gtctatacat gtgtaagact actaagagac atggcccacg tgtatgaaa ctcacagccc   1078
tctctcttga gcctgtacag gttgtgtata tgtaaagtcc ataggtgatg ttagattcat   1138
ggtgattaca caacggtttt acaattttgt aatgatttcc tagaattgaa ccagattggg   1198
agaggtattc cgatgcttat gaaaaactta cacgtgagct atggaagggg gtcacagtct   1258
ctgggtctaa cccctggaca tgtgccactg agaaccttga aattaagagg atgccatgtc   1318
attgcaaaga aatgatagtg tgaagggtta agttctttg aattgttaca ttgcgctggg   1378
acctgcaaat aagttctttt tttctaatga ggagagaaaa atatatgtat ttttatataa   1438
tgtctaaagt tatatttcag gtgtaatgtt ttctgtgcaa agttttgtaa attatatttg   1498
tgctatagta tttgattcaa aatatttaaa aatgtctcac tgttgacata tttaatgttt   1558
taaatgtaca gatgtattta actggtgcac tttgtaattc ccctgaaggt actcgtagct   1618
aaggggggcag aatactgttt ctggtgacca catgtagttt atttctttat tcttttaac    1678
ttaatagagt cttcag                                                   1694

<210> SEQ ID NO 8
<211> LENGTH: 316
<212> TYPE: PRT
```

<213> ORGANISM: Mus musculus

<400> SEQUENCE: 8

Met Arg Arg Ala Ser Arg Asp Tyr Gly Lys Tyr Leu Arg Ser Ser Glu
1               5                   10                  15

Glu Met Gly Ser Gly Pro Gly Val Pro His Glu Gly Pro Leu His Pro
            20                  25                  30

Ala Pro Ser Ala Pro Ala Pro Pro Pro Ala Ala Ser Arg Ser
        35                  40                  45

Met Phe Leu Ala Leu Leu Gly Leu Gly Leu Gln Val Val Cys Ser
50                  55                  60

Ile Ala Leu Phe Leu Tyr Phe Arg Ala Gln Met Asp Pro Asn Arg Ile
65                  70                  75                  80

Ser Glu Asp Ser Thr His Cys Phe Tyr Arg Ile Leu Arg Leu His Glu
                85                  90                  95

Asn Ala Asp Leu Gln Asp Ser Thr Leu Glu Ser Glu Asp Thr Leu Pro
            100                 105                 110

Asp Ser Cys Arg Arg Met Lys Gln Ala Phe Gln Gly Ala Val Gln Lys
        115                 120                 125

Glu Leu Gln His Ile Val Gly Pro Gln Arg Phe Ser Gly Ala Pro Ala
130                 135                 140

Met Met Glu Gly Ser Trp Leu Asp Val Ala Gln Arg Gly Lys Pro Glu
145                 150                 155                 160

Ala Gln Pro Phe Ala His Leu Thr Ile Asn Ala Ala Ser Ile Pro Ser
                165                 170                 175

Gly Ser His Lys Val Thr Leu Ser Ser Trp Tyr His Asp Arg Gly Trp
            180                 185                 190

Ala Lys Ile Ser Asn Met Thr Leu Ser Asn Gly Lys Leu Arg Val Asn
        195                 200                 205

Gln Asp Gly Phe Tyr Tyr Leu Tyr Ala Asn Ile Cys Phe Arg His His
210                 215                 220

Glu Thr Ser Gly Ser Val Pro Thr Asp Tyr Leu Gln Leu Met Val Tyr
225                 230                 235                 240

Val Val Lys Thr Ser Ile Lys Ile Pro Ser Ser His Asn Leu Met Lys
                245                 250                 255

Gly Gly Ser Thr Lys Asn Trp Ser Gly Asn Ser Glu Phe His Phe Tyr
            260                 265                 270

Ser Ile Asn Val Gly Gly Phe Phe Lys Leu Arg Ala Gly Glu Glu Ile
        275                 280                 285

Ser Ile Gln Val Ser Asn Pro Ser Leu Leu Asp Pro Asp Gln Asp Ala
290                 295                 300

Thr Tyr Phe Gly Ala Phe Lys Val Gln Asp Ile Asp
305                 310                 315

<210> SEQ ID NO 9
<211> LENGTH: 3154
<212> TYPE: DNA
<213> ORGANISM: Homo sapiens
<220> FEATURE:
<221> NAME/KEY: CDS
<222> LOCATION: (39)..(1904)
<223> OTHER INFORMATION:

<400> SEQUENCE: 9

```
ccgctgaggc cgcggcgccc gccagcctgt cccgcgcc atg gcc ccg cgc gcc cgg      56
                                         Met Ala Pro Arg Ala Arg
                                         1               5
```

-continued

| | | |
|---|---|---|
| cgg cgc cgc ccg ctg ttc gcg ctg ctg ctg ctc tgc gcg ctc ctg<br>Arg Arg Arg Pro Leu Phe Ala Leu Leu Leu Leu Cys Ala Leu Leu Leu<br>          10                    15                   20 | 104 |
| ctc tgc gcg ctg ctc gcc cgg ctg cag gtg gct ttg cag atc gct cct<br>Leu Cys Ala Leu Leu Ala Arg Leu Gln Val Ala Leu Gln Ile Ala Pro<br>          25                   30                   35 | 152 |
| cca tgt acc agt gag aag cat tat gag cat ctg gga cgg tgc tgt aac<br>Pro Cys Thr Ser Glu Lys His Tyr Glu His Leu Gly Arg Cys Cys Asn<br>40                      45                   50 | 200 |
| aaa tgt gaa cca gga aag tac atg tct tct aaa tgc act act acc tct<br>Lys Cys Glu Pro Gly Lys Tyr Met Ser Ser Lys Cys Thr Thr Thr Ser<br>55                      60                   65                   70 | 248 |
| gac agt gta tgt ctg ccc tgt ggc ccg gat gaa tac ttg gat agc tgg<br>Asp Ser Val Cys Leu Pro Cys Gly Pro Asp Glu Tyr Leu Asp Ser Trp<br>                    75                   80                   85 | 296 |
| aat gaa gaa gat aaa tgc ttg ctg cat aaa gtt tgt gat aca ggc aag<br>Asn Glu Glu Asp Lys Cys Leu Leu His Lys Val Cys Asp Thr Gly Lys<br>                   90                   95                  100 | 344 |
| gcc ctg gtg gcc gtg gtc gcc ggc aac agc acg acc ccc cgg cgc tgc<br>Ala Leu Val Ala Val Val Ala Gly Asn Ser Thr Thr Pro Arg Arg Cys<br>                 105                 110                115 | 392 |
| gcg tgc acg gct ggg tac cac tgg agc cag gac tgc gag tgc tgc cgc<br>Ala Cys Thr Ala Gly Tyr His Trp Ser Gln Asp Cys Glu Cys Cys Arg<br>120                    125                 130 | 440 |
| cgc aac acc gag tgc gcg ccg ggc ctg ggc gcc cag cac ccg ttg cag<br>Arg Asn Thr Glu Cys Ala Pro Gly Leu Gly Ala Gln His Pro Leu Gln<br>135                    140                 145                150 | 488 |
| ctc aac aag gac aca gtg tgc aaa cct tgc ctt gca ggc tac ttc tct<br>Leu Asn Lys Asp Thr Val Cys Lys Pro Cys Leu Ala Gly Tyr Phe Ser<br>                     155                 160                165 | 536 |
| gat gcc ttt tcc tcc acg gac aaa tgc aga ccc tgg acc aac tgt acc<br>Asp Ala Phe Ser Ser Thr Asp Lys Cys Arg Pro Trp Thr Asn Cys Thr<br>170                    175                 180 | 584 |
| ttc ctt gga aag aga gta gaa cat cat ggg aca gag aaa tcc gat gcg<br>Phe Leu Gly Lys Arg Val Glu His His Gly Thr Glu Lys Ser Asp Ala<br>185                    190                 195 | 632 |
| gtt tgc agt tct tct ctg cca gct aga aaa cca cca aat gaa ccc cat<br>Val Cys Ser Ser Ser Leu Pro Ala Arg Lys Pro Pro Asn Glu Pro His<br>200                    205                 210 | 680 |
| gtt tac ttg ccc ggt tta ata att ctg ctt ctc ttc gcg tct gtg gcc<br>Val Tyr Leu Pro Gly Leu Ile Ile Leu Leu Leu Phe Ala Ser Val Ala<br>215                    220                 225                230 | 728 |
| ctg gtg gct gcc atc atc ttt ggc gtt tgc tat agg aaa aaa ggg aaa<br>Leu Val Ala Ala Ile Ile Phe Gly Val Cys Tyr Arg Lys Lys Gly Lys<br>                     235                 240                245 | 776 |
| gca ctc aca gct aat ttg tgg cac tgg atc aat gag gct tgt ggc cgc<br>Ala Leu Thr Ala Asn Leu Trp His Trp Ile Asn Glu Ala Cys Gly Arg<br>250                    255                 260 | 824 |
| cta agt gga gat aag gag tcc tca ggt gac agt tgt gtc agt aca cac<br>Leu Ser Gly Asp Lys Glu Ser Ser Gly Asp Ser Cys Val Ser Thr His<br>265                    270                 275 | 872 |
| acg gca aac ttt ggt cag cag gga gca tgt gaa ggt gtc tta ctg ctg<br>Thr Ala Asn Phe Gly Gln Gln Gly Ala Cys Glu Gly Val Leu Leu Leu<br>280                    285                 290 | 920 |
| act ctg gag gag aag aca ttt cca gaa gat atg tgc tac cca gat caa<br>Thr Leu Glu Glu Lys Thr Phe Pro Glu Asp Met Cys Tyr Pro Asp Gln<br>295                    300                 305                310 | 968 |
| ggt ggt gtc tgt cag ggc acg tgt gta gga ggt ggt ccc tac gca caa<br>Gly Gly Val Cys Gln Gly Thr Cys Val Gly Gly Gly Pro Tyr Ala Gln | 1016 |

```
                    315                 320                 325
ggc gaa gat gcc agg atg ctc tca ttg gtc agc aag acc gag ata gag    1064
Gly Glu Asp Ala Arg Met Leu Ser Leu Val Ser Lys Thr Glu Ile Glu
            330                 335                 340 gaa gac agc ttc aga cag atg ccc aca gaa gat gaa tac atg gac agg    1112
Glu Asp Ser Phe Arg Gln Met Pro Thr Glu Asp Glu Tyr Met Asp Arg
        345                 350                 355 ccc tcc cag ccc aca gac cag tta ctg ttc ctc act gag cct gga agc    1160
Pro Ser Gln Pro Thr Asp Gln Leu Leu Phe Leu Thr Glu Pro Gly Ser
    360                 365                 370 aaa tcc aca cct cct ttc tct gaa ccc ctg gag gtg ggg gag aat gac    1208
Lys Ser Thr Pro Pro Phe Ser Glu Pro Leu Glu Val Gly Glu Asn Asp
375                 380                 385                 390 agt tta agc cag tgc ttc acg ggg aca cag agc aca gtg ggt tca gaa    1256
Ser Leu Ser Gln Cys Phe Thr Gly Thr Gln Ser Thr Val Gly Ser Glu
                395                 400                 405 agc tgc aac tgc act gag ccc ctg tgc agg act gat tgg act ccc atg    1304
Ser Cys Asn Cys Thr Glu Pro Leu Cys Arg Thr Asp Trp Thr Pro Met
            410                 415                 420 tcc tct gaa aac tac ttg caa aaa gag gtg gac agt ggc cat tgc ccg    1352
Ser Ser Glu Asn Tyr Leu Gln Lys Glu Val Asp Ser Gly His Cys Pro
        425                 430                 435 cac tgg gca gcc agc ccc agc ccc aac tgg gca gat gtc tgc aca ggc    1400
His Trp Ala Ala Ser Pro Ser Pro Asn Trp Ala Asp Val Cys Thr Gly
    440                 445                 450 tgc cgg aac cct cct ggg gag gac tgt gaa ccc ctc gtg ggt tcc cca    1448
Cys Arg Asn Pro Pro Gly Glu Asp Cys Glu Pro Leu Val Gly Ser Pro
455                 460                 465                 470 aaa cgt gga ccc ttg ccc cag tgc gcc tat ggc atg ggc ctt ccc cct    1496
Lys Arg Gly Pro Leu Pro Gln Cys Ala Tyr Gly Met Gly Leu Pro Pro
                475                 480                 485 gaa gaa gaa gcc agc agg acg gag gcc aga gac cag ccc gag gat ggg    1544
Glu Glu Glu Ala Ser Arg Thr Glu Ala Arg Asp Gln Pro Glu Asp Gly
            490                 495                 500 gct gat ggg agg ctc cca agc tca gcg agg gca ggt gcc ggg tct gga    1592
Ala Asp Gly Arg Leu Pro Ser Ser Ala Arg Ala Gly Ala Gly Ser Gly
        505                 510                 515 agc tcc cct ggt ggc cag tcc cct gca tct gga aat gtg act gga aac    1640
Ser Ser Pro Gly Gly Gln Ser Pro Ala Ser Gly Asn Val Thr Gly Asn
    520                 525                 530 agt aac tcc acg ttc atc tcc agc ggg cag gtg atg aac ttc aag ggc    1688
Ser Asn Ser Thr Phe Ile Ser Ser Gly Gln Val Met Asn Phe Lys Gly
535                 540                 545                 550 gac atc atc gtg gtc tac gtc agc cag acc tcg cag gag ggc gcg gcg    1736
Asp Ile Ile Val Val Tyr Val Ser Gln Thr Ser Gln Glu Gly Ala Ala
                555                 560                 565 gcg gct gcg gag ccc atg ggc cgc ccg gtg cag gag gag acc ctg gcg    1784
Ala Ala Ala Glu Pro Met Gly Arg Pro Val Gln Glu Glu Thr Leu Ala
            570                 575                 580 cgc cga gac tcc ttc gcg ggg aac ggc ccg cgc ttc ccg gac ccg tgc    1832
Arg Arg Asp Ser Phe Ala Gly Asn Gly Pro Arg Phe Pro Asp Pro Cys
        585                 590                 595 ggc ggc ccc gag ggg ctg cgg gag ccg gag aag gcc tcg agg ccg gtg    1880
Gly Gly Pro Glu Gly Leu Arg Glu Pro Glu Lys Ala Ser Arg Pro Val
    600                 605                 610 cag gag caa ggc ggg gcc aag gct tgagcgcccc ccatggctgg gagcccgaag   1934
Gln Glu Gln Gly Gly Ala Lys Ala
615                 620 ctcggagcca gggctcgcga gggcagcacc gcagcctctg ccccagcccc ggccacccag  1994
```

```
ggatcgatcg gtacagtcga ggaagaccac ccggcattct ctgcccactt tgccttccag    2054
gaaatgggct tttcaggaag tgaattgatg aggactgtcc ccatgcccac ggatgctcag    2114
cagcccgccg cactgggggca gatgtctccc ctgccactcc tcaaactcgc agcagtaatt   2174
tgtggcacta tgacagctat ttttatgact atcctgttct gtggggggggg ggtctatgtt   2234 ttcccccccat atttgtattc cttttcataa cttttcttga tatctttcct ccctcttttt   2294
taatgtaaag gttttctcaa aaattctcct aaaggtgagg gtctctttct tttctctttt   2354 ccttttttt  ttcttttttt ggcaacctgg ctctggccca ggctagagtg cagtggtgcg    2414
attatagccc ggtgcagcct ctaactcctg ggctcaagca atccaagtga tcctcccacc   2474
tcaaccttcg gagtagctgg gatcacagct gcaggccacg cccagcttcc tcccccgac    2534 tcccccccc  cagagacacg gtcccaccat gttacccagc ctggtctcaa actccccagc   2594
taaagcagtc ctccagcctc ggcctcccaa agtactggga ttacaggcgt gagcccccac   2654
gctggcctgc tttacgtatt tctttttgtg cccctgctca cagtgtttta gagatggctt   2714
tcccagtgtg tgttcattgt aaacactttt gggaaagggc taaacatgtg aggcctggag   2774
atagttgcta agttgctagg aacatgtggt gggactttca tattctgaaa aatgttctat   2834
attctcattt ttctaaaaga aagaaaaaag gaaacccgat ttatttctcc tgaatctttt   2894
taagtttgtg tcgttcctta agcagaacta agctcagtat gtgaccttac ccgctaggtg   2954
gttaatttat ccatgctggc agaggcactc aggtacttgg taagcaaatt tctaaaactc   3014
caagttgctg cagcttggca ttcttcttat tctagaggtc tctctggaaa agatggagaa   3074
aatgaacagg acatgggggct cctggaaaga aagggcccgg gaagttcaag gaagaataaa   3134
gttgaaattt taaaaaaaaa                                               3154
```

<210> SEQ ID NO 10
<211> LENGTH: 622
<212> TYPE: PRT
<213> ORGANISM: Homo sapiens

<400> SEQUENCE: 10

Met Ala Pro Arg Ala Arg Arg Arg Pro Leu Phe Ala Leu Leu Leu
1               5                   10                  15

Leu Cys Ala Leu Leu Leu Leu Cys Ala Leu Leu Ala Arg Leu Gln Val
            20                  25                  30

Ala Leu Gln Ile Ala Pro Pro Cys Thr Ser Glu Lys His Tyr Glu His
            35                  40                  45

Leu Gly Arg Cys Cys Asn Lys Cys Glu Pro Gly Lys Tyr Met Ser Ser
        50                  55                  60

Lys Cys Thr Thr Thr Ser Asp Ser Val Cys Leu Pro Cys Gly Pro Asp
65                  70                  75                  80

Glu Tyr Leu Asp Ser Trp Asn Glu Glu Asp Lys Cys Leu Leu His Lys
                85                  90                  95

Val Cys Asp Thr Gly Lys Ala Leu Val Ala Val Ala Gly Asn Ser
            100                 105                 110

Thr Thr Pro Arg Arg Cys Ala Cys Thr Ala Gly Tyr His Trp Ser Gln
            115                 120                 125

Asp Cys Glu Cys Cys Arg Arg Asn Thr Glu Cys Ala Pro Gly Leu Gly
        130                 135                 140

Ala Gln His Pro Leu Gln Leu Asn Lys Asp Thr Val Cys Lys Pro Cys
145                 150                 155                 160

-continued

```
Leu Ala Gly Tyr Phe Ser Asp Ala Phe Ser Thr Asp Lys Cys Arg
                165                 170                 175

Pro Trp Thr Asn Cys Thr Phe Leu Gly Lys Arg Val Glu His His Gly
            180                 185                 190

Thr Glu Lys Ser Asp Ala Val Cys Ser Ser Leu Pro Ala Arg Lys
        195                 200                 205

Pro Pro Asn Glu Pro His Val Tyr Leu Pro Gly Leu Ile Ile Leu Leu
    210                 215                 220

Leu Phe Ala Ser Val Ala Leu Val Ala Ala Ile Ile Phe Gly Val Cys
225                 230                 235                 240

Tyr Arg Lys Lys Gly Lys Ala Leu Thr Ala Asn Leu Trp His Trp Ile
                245                 250                 255

Asn Glu Ala Cys Gly Arg Leu Ser Gly Asp Lys Glu Ser Ser Gly Asp
            260                 265                 270

Ser Cys Val Ser Thr His Thr Ala Asn Phe Gly Gln Gln Gly Ala Cys
        275                 280                 285

Glu Gly Val Leu Leu Leu Thr Leu Glu Glu Lys Thr Phe Pro Glu Asp
    290                 295                 300

Met Cys Tyr Pro Asp Gln Gly Val Cys Gln Gly Thr Cys Val Gly
305                 310                 315                 320

Gly Gly Pro Tyr Ala Gln Gly Glu Asp Ala Arg Met Leu Ser Leu Val
                325                 330                 335

Ser Lys Thr Glu Ile Glu Glu Asp Ser Phe Arg Gln Met Pro Thr Glu
            340                 345                 350

Asp Glu Tyr Met Asp Arg Pro Ser Gln Pro Thr Asp Gln Leu Leu Phe
        355                 360                 365

Leu Thr Glu Pro Gly Ser Lys Ser Thr Pro Pro Phe Ser Glu Pro Leu
    370                 375                 380

Glu Val Gly Glu Asn Asp Ser Leu Ser Gln Cys Phe Thr Gly Thr Gln
385                 390                 395                 400

Ser Thr Val Gly Ser Glu Ser Cys Asn Cys Thr Glu Pro Leu Cys Arg
                405                 410                 415

Thr Asp Trp Thr Pro Met Ser Ser Glu Asn Tyr Leu Gln Lys Glu Val
            420                 425                 430

Asp Ser Gly His Cys Pro His Trp Ala Ala Ser Pro Ser Pro Asn Trp
        435                 440                 445

Ala Asp Val Cys Thr Gly Cys Arg Asn Pro Pro Gly Glu Asp Cys Glu
    450                 455                 460

Pro Leu Val Gly Ser Pro Lys Arg Gly Pro Leu Pro Gln Cys Ala Tyr
465                 470                 475                 480

Gly Met Gly Leu Pro Pro Glu Glu Ala Ser Arg Thr Glu Ala Arg
                485                 490                 495

Asp Gln Pro Glu Asp Gly Ala Asp Gly Arg Leu Pro Ser Ser Ala Arg
            500                 505                 510

Ala Gly Ala Gly Ser Gly Ser Ser Pro Gly Gly Gln Ser Pro Ala Ser
        515                 520                 525

Gly Asn Val Thr Gly Asn Ser Asn Ser Thr Phe Ile Ser Ser Gly Gln
    530                 535                 540

Val Met Asn Phe Lys Gly Asp Ile Ile Val Val Tyr Val Ser Gln Thr
545                 550                 555                 560

Ser Gln Glu Gly Ala Ala Ala Ala Glu Pro Met Gly Arg Pro Val
                565                 570                 575

Gln Glu Glu Thr Leu Ala Arg Arg Asp Ser Phe Ala Gly Asn Gly Pro
```

```
            580                 585                 590
Arg Phe Pro Asp Pro Cys Gly Gly Pro Glu Gly Leu Arg Glu Pro Glu
    595                 600                 605

Lys Ala Ser Arg Pro Val Gln Glu Gln Gly Gly Ala Lys Ala
    610                 615                 620
```

<210> SEQ ID NO 11
<211> LENGTH: 3591
<212> TYPE: DNA
<213> ORGANISM: Mus musculus
<220> FEATURE:
<221> NAME/KEY: misc_feature
<222> LOCATION: (48)..(48)
<223> OTHER INFORMATION: "n" = a, t, c, g
<221> NAME/KEY: misc_feature
<222> LOCATION: (50)..(50)
<223> OTHER INFORMATION: "n" = a, t, c, g
<221> NAME/KEY: misc_feature
<222> LOCATION: (52)..(52)
<223> OTHER INFORMATION: "n" = a, t, c, g

<400> SEQUENCE: 11

| | | | | | |
|---|---|---|---|---|---|
| tggtggtgca | cgcctttaat | cccagcgctt | gggaggcaga | ggcaggcngn | tntctgagtt | 60 |
| cgaggccagt | ctggtctaca | gagagagttc | caggacagcc | aggactacac | agagaaaccc | 120 |
| tgtctttaaa | acaaaaacca | agcaaccaaa | caagaagagc | aacaataaaa | attgagcatc | 180 |
| ctcactaacg | gtttgagtat | tgatgaaac | ttttggacca | tttataaaga | aaactcaaca | 240 |
| cacaccagag | gctcttctct | tcccactcac | ccagggaaca | tttggtaaca | tcaatggttg | 300 |
| tcacaatggg | tatgggtggt | gctgctggca | ctaggaggaa | gggagggtga | ggacacctct | 360 |
| agacacactg | cagtgtctgg | ggacatcccc | aaacaaagga | ccacagcccc | aaggataaag | 420 |
| atgccaagct | tgatgagtgt | ggtggggcat | ctttaatccc | atcactcagg | aggcagaggc | 480 |
| aggggggatct | ctatgagttg | gaggccaggc | tggtccacac | agcaaaatct | aggccagcca | 540 |
| ggtctccata | gtgggaccct | gcctcaaaaa | caaaaccaag | ggtgtagagc | tcaagaaaca | 600 |
| agacatacat | agacatgaca | tatggtatag | atgtggcata | ctgcatagat | gtgcatcta | 660 |
| acacagacgg | aacacaccac | atagacatga | catggtatag | atgtgacata | ctgcatagat | 720 |
| gtgacatcta | acacagactg | gacacaccac | gtagacatga | catatatgtg | acatacaaca | 780 |
| cagatgacat | atggcataga | tgtgacatat | aacagatgta | acataccata | cagataggac | 840 |
| atacatacat | acatacatac | atacatagat | gtgacatata | acagagccat | ggcatagtgc | 900 |
| atagacatca | catccacatg | ttcagcatcc | ttaacgcagt | tgctggcaag | atgggaatac | 960 |
| tgcatagatt | cctctgaagt | tcttgtctgt | cacctcgacg | gagatcagga | tgggaggtcc | 1020 |
| tcttatttg | tttccatttc | aaatcttgta | ttagtctttg | gccccacagt | cccaggtctg | 1080 |
| taatatggtt | accctgggac | cctgtcttca | gcatgtgacc | cctcaaaatc | ctgagcctcc | 1140 |
| agccttatcg | tactaaggta | gcaggggaag | agaagggttc | aggtggcaaa | gccctggaaa | 1200 |
| cccacccatt | tcattcacct | gtactctgat | ccgctccgtc | cccacagcag | atgagaatct | 1260 |
| tgtaccctgg | ctctctggtt | ttgtttgttt | gtttgttttg | ttttgttttg | ttttgttttt | 1320 |
| tgttttgttt | tgttttgttt | ttcgagacaa | ggtttctctg | tatagccctg | gctgtcctgg | 1380 |
| aactcacttc | gtagaccagg | ctggcctcga | actcagaaat | ctgcctgcct | ctgcctccca | 1440 |
| agtgctggga | ttaaaggcgt | gcaccaccag | atcacgggga | cctgagatca | tgggcaagtc | 1500 |
| ccttgactgc | tctgagttga | agtttcctat | tccagaaaag | ccagagttac | ctcccaaact | 1560 |
| aaccttgtta | gccaggcata | gtgtgcacac | ctatgacaca | gcgcttggga | ggcagaggca | 1620 |

```
ggggatggga gttcagcaca agcctgactt ccaattggac tttgtctcaa tagatggagg    1680
gtgggctggg gaaatggcca agtgggtcag agcattcatt gtagaagcag gaggacccga    1740
cttcggagct acaacatcca cgtaaacagc tgggtgcggc acctacttgc tcacctccaa    1800
cactgacaga tggagactct gagacagggt taccaaggct tgctggcggc cagcctggct    1860
gcaaatccct gggctcttaa gtttaggag actctgcctc aaaggaacaa aaggaaagat     1920
gacagagggg gacagccaac atctcctctt gccttggcag tcatggatgt gtgtccctgc    1980
acacacacat atgcacacac acacacaaac acacacacac acaaacacac acacacaa     2040 acacacacac acacacacac acacgcacac acacacta aaacaaatta acaaacaaaa     2100
acaaggacta ggaacagctc agttgtagag tacttgccta gcatgtgtga gaccctagag    2160
gcttgggcat acacacacac acacattcat acacagacac agactcacat atggacacac    2220
acacagtctc acacatatgg gatagcaata tataggagag ttttgtagag agcgtatcac    2280
aacgtccaac acaataaatc aaaaagtga atgatcactg cggcctggag gtgaaatgcc    2340
ttgcccaagg tggttgggaa atgacgaggt tgggaaatgg tagacccaga actgcaattc    2400
agtgctggag ctcaccagtg agaagcatct aagagaagct tgggagaaca cccagctctc    2460
tctctccggc tcacaggtct gttcgttggg aagcacatga aggtctgggc acacaggagg    2520
cttagtcaga acagcttgct gaagacagat caaggccccg ctccaccatg gtggcaggcg    2580
aggaggatgg aaggccgggg gctgccggct gttggcaaga ctgtgccaaa gctttcctga    2640
gtggagcagg gcagggctgg aggaggggaa gggtccatga cgatctcaca gctcgggaga    2700
ggaaggtgtt tgccccatcc aggtcacccc aaggcttaga gccaagaccc cagtctccta    2760
atttccaatc acaaacctga caccatcaac tgaggtctcg tgaacactgc taaaagtggt    2820
ttttctgtgt ttcgagagtc tcattttatc ctcagatcaa tatagggaca aaggcttgag    2880
cgacaaaggg tctgttttg ttctttaaac agaagaggaa ggatagtgct agcctgagaa     2940
ggatgaagct tctgcttgct cccacatgtg tgtgtccccc cgccccccag gctcatcttt    3000
ccttccccaa ggagtcagcc tgctggagct aggggtttgc cccgtggaat tccccaaatc    3060
ctgcctcaaa gagcctgctc ccagaggcca ggagaggaag ctgagtcaaa gactctatca    3120
gggggcgggg atgagaggat agaacctaca gtgtggggag gggctccagg ctgcactctg    3180
gccagggagg gggtgtctca gaagcccaag gaagaggggt ctcaggcctc aggtctccca    3240
gtcttttact gggctgatca gtcagggccg tcagacctag gctaggtga atgccccatt     3300 ctgcacaccc tccttcccct tcccacaaag tctgcagttt gcagaaacta aaccctgagt    3360
tctgtggttt cctgtgggtc tgggggtcct gcctgacttg gcaatggggg actgtggaca    3420
gggcataagg gagggggtag tgtaaacaca cacacacaca cacacacaca cacacacaca    3480
cgctgagtca gcataagcct ggaggggagg gcgggggtca ctgattcagt tttactgcct    3540 cttttaaaatc tctgcaaagg cagcgttagc cagaagctgc ggtcctcacc a           3591
```

<210> SEQ ID NO 12
<211> LENGTH: 1991
<212> TYPE: DNA
<213> ORGANISM: Mus musculus

<400> SEQUENCE: 12

```
cccgggtctc ccttaactcc tgggactctg aaccttggag gcgaggcgca ggtaatggct      60
gaggcaggat tggggcgggg aaaccgaggc acccgccctc tgcaactctg gactctgtag     120
```

-continued

```
ggcaggcagg gagccgtggg gacaggctgg cccgcgccgc ctcttcccaa ctcgtgcagc      180
ccggagcgac ccgccgcgaa tccgcagctc agttgggtag cacagcttgt cctgaccca       240 ccgccaaggt gagactcgcc cgccagccct tgctctgcct cccacgggga gggtctctg       300 tctgttgggg ccacccact tccttcctgt tcgcctctac tgagaggtgc gagtgggaa        360 tgcaaggcaa actcttcgct gggtgacctg gggtgagtcg ctgaccctct ctgagccttt      420
atgcaaagca cggaacgaga gattccagaa tccgagcttg cagggaccgg aggggttggt      480
ggtgagtgtt caaggaagga gtctggaaag attgggcggc ttgtgaagtt aaggagggag      540
gggaggaggt gggaagctgg ccacacccac cacagcgctg ggctctgcgg tcgaaacagc      600
ctgcagctgc tgtaggtgcc aaggtcaaaa ggctacagcc agccacgtgg tgtgtgcctt      660
ctggaagttc cttaggctgg aaaccgggtg tgggaaaggc catggaagag tgtggacaga      720
acttcctgga aaaggcagtt attgctgctg tttatgatgg cgaggggaa ctcggagaca       780 gtcccacact tagatgactc cagatacaca atttgcacta ggacttacaa aacacagagg      840
agacaggggg ctgttacatg gcgccacag aggaattatt taggcctgta attccaacac       900 ttgaagtgg ctcatctttg ctacccagg aggaagtta gggatagcct gggcttcttg         960
agacactgtc tcaaaacaaa acaaaaaaa aaaaataat tggagtgtat gtcacaggca       1020
agccactgag gttcccatgc tagagtcgag acacccaccc agaaaaagtg acagcgagtt     1080
acagacagcc aagggtgtga aaacacagac gttcagccta aacagcctc agtgcagtga     1140 acagtcaaac tcgggaccta cagatgccca gtacacatta ccatcagacc ctggctgact     1200
gtgctggctt cgagaaactt ttcacggctc agtctggcct gggtgccccg ccccagcccc     1260
atttccagtt ctggggaagt ccagtgctca catgaccaag ggggagggctt ctggacaatc     1320 ctcggagaaa atgcatcatc tttcccaatg atgcacttct gccccagaga ataaagactc     1380
ggtgatcacc gcttttggtc caggagctta actgcctctt gcagcctctc tgaccacctg     1440
tgcttcctcc agggtaagtg tcagaggagc gaggtggaag aggcctgtgg gggccacctt     1500
cccagctcct cagctccttg caggcccaat tgctactggt gtgtctgtgg aactgacggc     1560
tgtagatggc tagggtgtgt gtgtgtgtgt gtgtgtgtgt gtgtgtgtgt cttaagaccg     1620
gtcttatgtc tttatctcag actttctgtt tccatttttc aaacttccca atgtagctga     1680
ggctggcctt gaacttctgg tccagttgct ccacctccat ggtagtgcct gagtttatag     1740
gcatgcaccg tgagaccagg ctcagcgggc tagtctttct ttgcttggac cagggtctcg     1800
ctctctgtcc tcaccagaga ctctgaactc cctctcttcc tcacagatgg attcatgggt     1860
ggtgctgctg ggcctacaaa tcatatggct cccactcctg acccacggta cagcccccac     1920
tcccaccctg agatttgtgg ctgtgggcga ctggggaggg tccccaatg ccccattcca      1980 cacagcccgg g                                                         1991
```

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Lys Val Glu Lys Ile Gly Glu Gly Thr Tyr Gly Val Val Tyr Lys
1               5                   10                  15